(12) United States Patent
Goldstein et al.

(10) Patent No.: US 9,273,338 B2
(45) Date of Patent: Mar. 1, 2016

(54) CHIMERIC AVIAN-BASED SCREENING SYSTEM CONTAINING MAMMALIAN GRAFTS

(71) Applicants: BAR ILAN UNIVERSITY, Ramat Gan (IL); MEDICAL RESEARCH FUND OF TEL-AVIV SOURASKY MEDICAL CENTER, Tel-Aviv (IL)

(72) Inventors: Ron Goldstein, Jerusalem (IL); Tamar Tennenbaum, Jerusalem (IL); Varda Deutsch, Jerusalem (IL)

(73) Assignees: Bar Ilan University, Ramat Gan (IL); Medical Research Fund of Tel-Aviv Sourasky Medical Center, Tel Aviv (IL)

(*) Notice: Subject to any disclaimer, the term of this patent is extended or adjusted under 35 U.S.C. 154(b) by 281 days.

(21) Appl. No.: 13/693,013

(22) Filed: Dec. 3, 2012

(65) Prior Publication Data

US 2013/0171680 A1    Jul. 4, 2013

Related U.S. Application Data

(62) Division of application No. 11/571,343, filed as application No. PCT/IL2005/000687 on Jun. 28, 2005, now Pat. No. 8,324,447.

(60) Provisional application No. 60/582,807, filed on Jun. 28, 2004.

(51) Int. Cl.
*A01K 67/00* (2006.01)
*A01K 67/027* (2006.01)
*G01N 33/00* (2006.01)
*C12N 5/00* (2006.01)
*C12Q 1/02* (2006.01)
*G01N 33/50* (2006.01)

(52) U.S. Cl.
CPC ............ *C12Q 1/025* (2013.01); *A01K 67/0271* (2013.01); *G01N 33/5088* (2013.01); *A01K 2227/105* (2013.01); *A01K 2227/106* (2013.01); *A01K 2227/30* (2013.01); *A01K 2267/03* (2013.01); *C12N 2799/022* (2013.01); *G01N 2500/00* (2013.01); *G01N 2800/52* (2013.01)

(58) Field of Classification Search
CPC . G01N 33/5088; C12Q 1/025; A01K 67/0271
USPC .......................................................... 800/10
See application file for complete search history.

(56) References Cited

U.S. PATENT DOCUMENTS

| | | | |
|---|---|---|---|
| 5,512,475 A | 4/1996 | Naughton et al. | |
| 5,807,746 A | 9/1998 | Lin et al. | |
| 5,888,720 A | 3/1999 | Mitrani | |
| 6,228,345 B1* | 5/2001 | Ossowski | 424/9.1 |
| 2002/0151004 A1 | 10/2002 | Craig | |
| 2003/0175328 A1 | 9/2003 | Shefer et al. | |

OTHER PUBLICATIONS

Shearman et al., 1980, Int. J. Cancer 25:263-269.*
Kunzi-Rappb et al., 1999, Arch. Dermatol. Res. 291:290-295.*
Armstrong et al 1982; Cancer Research 42:1826-1837.*
Laurin et al 2004, Mund Kiefer gesichtschir. 8:223-228.*
Mostafa et al 1980, Pathology 132:191-205.*
Backvall. H. et al., "Similar UV responses are seen in a skin organ culture as in human skin in vivo", Exp Dermatol., 11(4):349-56 (2002).
Borges, J. et al., "Chorioallantoic membrane angiogenesis model for tissue engineering: a new twist on a classic model", Tissue Eng; 9(3):441-50 (2003).
Cashman, J.D. et al., "Kinetic evidence of the regeneration of multilineage hematopoiesis from primitive cells in normal human bone marrow transplanted into immunodeficient mice", Blood, 89(12):4307-4316 (Jun. 15, 1997).
Dazzi, F. et al., "Normal and chronic phase CML hematopoietic cells repopulate NOD/SCID bone marrow with different kinetics and cell lineage representation", Hematol J., 1(5):307-315 (2000).
Djabari, Z. et al., "Human skin grafting onto chorioallantoic membrane of chick embryo, using the interposition technique: histological studies and comparison to an ex vivo model", Journal of Investigative Dermatology, 121(1), 0505 (abstract only) (Jul. 2003).
Fisher, C. J., "Chick Embryos in Shell-less Culture", pp. 105-115, in Tested studies for laboratory teaching, vol. 5 (C.A. Goldman, P.L. Hauta, M.A. O'Donnell, S. E. Andrews, and R. van der Heiden, Editors). Proceedings of the 5th Workshop/Conference of the Association for Biology Laboratory Education (ABLE).
Ghazizadeh, S. et al., "Durable and stratum-specific gene expression in epidermis", Gene Ther, 9(19):1278-85 (Oct. 2002).
Goodpasture, E. W. et al., "A study of human skin grafted upon the chorio-allantois of chick embryos", J. Exp. Med., 68:891-904 (1938).
Hamamichi, S. et al., "Establishment of a chick embryo shell-less culture system and its use to observe change in behavior caused by nicotine and substances from cigarette smoke", Toxicology Letters, 119(2):95-102 (Feb. 2001).
Klueh, U. et al., "Ex ova chick chorioallantoic membrane as a novel model for evaluation of tissue responses to biomaterials and implants", J Biomed Mater Res A., 67(3):838-843 (Dec. 2003).
Lutzko, C. et al., "Human hematopoietic progenitors engraft in fetal canine recipients and expand with neonatal injection of fibroblasts expressing human hematopoietic cytokines", Exp Hematol., 30(7):801-808 (Jul. 2002).
Miyake, S. et al, "Efficient generation of recombinant adenoviruses using adenovirus DNA-terminal protein complex and a cosmid bearing the full-length virus genome", Proc Natl Acad Sci U S A., 93(3)1320-1324 (Feb. 1996).

(Continued)

*Primary Examiner* — Scott Long
*Assistant Examiner* — Kelaginamane T Hiriyanna
(74) *Attorney, Agent, or Firm* — Rodney J. Fuller; Booth Udall Fuller, PLC

(57) ABSTRACT

The present invention relates to animal model systems comprising a chimera between an avian embryo and a mammalian organism. Specifically, chimeric model systems comprising normal, diseased or genetically transformed mammalian cells and tissues transplanted into avian embryos, and uses thereof for in vivo testing of drugs and therapeutic modalities are disclosed.

10 Claims, 19 Drawing Sheets

(56) References Cited

OTHER PUBLICATIONS

Mortell, A. et al., "Adriamycin effects on the chick embryo", Pediatr Surg Int., 19(5):359-364 (Jul. 2003).

Kunzi-Rapp, K. et al., "Increased blood levels of human S100 in melanoma chick embryo xenografts' circulation", Pigment Cell Res., 14(1):9-13 (Feb. 2001).

Kunzi-Rapp, K. et al., "Test System for Human Tumor Cell Sensitivity to Drugs on Chicken Chorioallantoic Membranes", In vitro. Cell. Dev. Biol., pp. 565-566 (1992).

Reams, W. M. et al., "A developmental study of murine epidermal Langerhans cells", Developmental Biology, pp. 114-123 (1973).

Reubinoff, B.E. et al., "Neural progenitors from human embryonic stem cells", Nat Biotechnol., 19(12):1134-1140 (Dec. 2001).

Roux, E. et al., Skin iRoux, E. et al., "Skin interposition-grafting onto the chorioallantoic membrane of chick embryo as a model for wound healing studies", Journal of Investigative Dermatology, 121(1), 0500 (abstract only) (Jul. 2003).

Trainer, A.H. et al., "Gene delivery to the epidermis", Hum Mol Genet., 6(10):1761-1767 (1997).

Tufan, A. et al., "Shell-less culture of the chick embryo as a model system in the study of developmental neurobiology", Neuroanatomy, 3:8-11 (2004).

Valdes, T.I. et al., "The chick chorioallantoic membrane as a novel in vivo model for the testing of biomaterials", J Biomed Mater Res., 62(2):273-282 (Nov. 2002).

Yahata T. et al., "A highly sensitive strategy for SCID-repopulating cell assay by direct injection of primitive human hematopoietic cells into NOD/SCID mice bone marrow", Blood, 101(8):2905-2913 (Apr. 15, 2003).

International Search Report for PCT/IL2005/000687 dated Apr. 24, 2006.

Written Opinion of the International Searching Authority for PCT/IL2005/000687 dated Apr. 24, 2006.

International Preliminary Report on Patentability for PCT/IL2005/000687 dated Dec. 28, 2006.

Christanson, S. W. et al., "Enhanced human CD4+ T cell engraftment in beta2-microglobulin-deficient NOD-scid mice", J. Immunol., 158(8):3578-3586 (1997).

Frankenburg, Shoshana et al., "Recombinant hydrophilic human gp100: update by dendritic cells and stimulation of autologous CD8+ lymphocytes from melanoma patients", Immunol. Lett., 15:94(3):253-259 (2004).

Gavrieli, Yael et al., "Identification of programmed cell death in situ via specific labeling of nuclear DNA fragmentation", J. Cell. Biol., 119(3):493-501 (1992).

Kook, Yoon Hoh et al., "The effect of antisense inhibition of urokinase receptor in human squamous cell carcinoma on malignancy", The EMBO Journal, 13(17):3983-3991 (1994).

Longenecker, B. M. et al., "A new class of infectious agents detectable by the production of chorioallantoic membrane lesions by human lymphoblastoid cell lines and their culture supernatants", J. Natl., Cancer Inst., 58(4):853-862 (1977).

Pinkus, Hermann, "Examination of the epidermis by the strip method of removing horny layers. I. Observations on thickness of the horny layer, and on mitotic activity after stripping", J. Invest. Dermatol., 16(6):383-386 (1951).

Webster, Guy F., "Acne Vulgaris: State of the Science", Arch. Dermatol., 135(9):1101-1102 (1999).

Zanjani, Esmail D. et al., "Human-ovine xenogenic transplantation of stem cells in utero", Bone Marrow Transplant, 9(Suppl 1):86-89 (1992).

* cited by examiner

US 9,273,338 B2

CHIMERIC AVIAN-BASED SCREENING SYSTEM CONTAINING MAMMALIAN GRAFTS

RELATED APPLICATION DATA

This application is a divisional of U.S. application Ser. No. 11/571,343, filed Dec. 27, 2006, now U.S. Pat. No. 8,324,447, issued Dec. 4, 2012, which is the U.S. National Stage of International Application No. PCT/IL2005/000687, filed Jun. 28, 2005, which claims the benefit of U.S. Provisional Application No. 60/582,807, filed Jun. 28, 2004, the contents of each of which are herein expressly incorporated by reference for all purposes.

FIELD OF THE INVENTION

The present invention relates to chimeric model systems comprising mammalian grafts transplanted into avian embryos, useful for in vivo testing of drugs and novel therapeutic modalities of human diseases and disorders.

BACKGROUND OF THE INVENTION

The embryonic chick is a widely used model for studying various biological processes. The low cost and easy availability of this system provide major advantages compared to in vivo systems utilizing sentient animals. In addition, many in vivo systems, particularly model systems for studying human tissues and organs, require transplanting an examined graft in an immune compromised animal, in order to avoid graft rejection. Such animals, for example severe combined immune deficient (SCID) mice, are expensive, sickly and hard to maintain. The development of simple, cost-effective systems for mammalian explants is therefore desirable.

The skin is a complex three-dimensional organ that covers the exterior of the body. It is our first line of protection from the myriad microorganisms in our environment, prevents us from dehydrating, and is critically involved in body heat regulation. In addition, a specialized modification of the skin, the hair, is of vital social and psychological importance. Because the skin and hair are very often affected by disease, mechanical and heat damage, there is considerable interest in the mechanisms involved in various physiological or pathophysiological processes associated with human skin and hair. There is a need to research dermatological processes such as the influence of cosmetics and environmental substances on skin, as well as wound healing in the absence and the presence of pharmaceutical and environment substances.

Because the study of human skin in vivo is limited for ethical and medical reasons, most current strategies for the testing of therapies for treating skin damage and disease involve the extensive use of experimental animals. It is common, for example, to investigate the toxicological properties of topically administered materials such as therapeutic formulations or cosmetics by applying the substance to the skin of an experimental animal. Animal studies have also played an important role in preclinical trials of compounds involved in wound healing. Another technique involving the use of experimental animals to study intact human skin is the use of a Non-obese diabetic Severe Combined Immunodeficiency (NOD-SCID) mouse for the long term observation of human skin xenografts.

Animal testing often entails great expense, and involves many legal and ethical issues. Although it is possible to study some properties of human skin cells using cell cultures as disclosed in U.S. Pat. No. 5,512,475 or in vitro micro-organs as disclosed in U.S. Pat. No. 5,888,720, these models require using a population of diffusion nourished skin cells. These models therefore lack important features of skin physiology, such as circulating blood cells that can participate in inflammation and in wound healing. Furthermore, most in-vitro systems require that the epidermis be submerged in medium rather than exposed to air, precluding the possibility of using these systems to conduct experiments with topical treatments such as detergents, cosmetics, radiation, or topically applied pharmaceutical compositions.

It would be advantageous to have a realistic ex vivo model of intact human skin to obviate the need for using experimental animals or recruiting human volunteers. The chick embryo has been used as an in vivo model for the investigation of a number of biological systems for over a century, and has been favored for its simplicity, easy availability, immunodeficient properties, and for the highly vascularized structure of the CAM. For example, the Hen's Egg Test-Chorioallantoic Membrane (HET-CAM) assay is a well-known method for screening the irritancy potential of topically applied compositions such as cosmetics.

The first disclosure of the grafting of human skin upon the chorioallantois of chick embryos was reported by Goodpasture et al. in 1938 (J Exp Med 68:891-904). Goodpasture et al. disclosed the grafting of human and other animal (rabbit, chicken) skin upon the CAM of chick embryos, Goodpasture et al. reported that the epithelium of the chorioallantois fuses with that of the graft, the collagen fibers of the corium interlace with those of the membrane after the separation or disappearance of the ectodermal layer, and the blood vessels of the chick anastomose with those of the graft. This vascular communication between the two tissues is largely responsible for the nourishment of the graft by affording a plasmatic circulation. No laboratory or clinical applications of the system were disclosed by Goodpasture et al. They reported that their human skin grafts may be experimentally infected with viruses, though no details or experimental data were provided.

More recently, after a 60 year period during which there seems to be a dearth of relevant publications, Kunzi-Rapp et al. 1999 (Kunzi-Rapp K, Rück A, Kaufmann R. 1999. Arch Dermatol Res. 291, 290-295) published a study where human skin was grafted to the CAM of chicken eggs. They reported histological and immunohistochemistry results showing the revascularization after 2 to 3 days by reperfusion of pre-existing graft vasculature as well as differentiated human epidermis and dermis containing all cellular and extracellular constituents such as skin immune cells. Based upon these findings, the authors speculated that the CAM system could be used as an alternative system to animal models for studying regulation of cell adhesion molecules, angiogenesis in initial wound healing, and skin toxicology, though none of these were demonstrated.

A modified CAM-based system for investigating wound healing is presented in Roux et al. 2003A (Roux, E.; Domloge, N.; Djabari, Z.; Dal Farra, C.; Bauza, E. 2003. Journal of Investigative Dermatology 121:1, 0500-0501) and Roux et al. 2003B (Roux, E.; Domloge, N.; Djabari, Z.; Dal Farra, C.; Bauza, E. 2003. Journal of Investigative Dermatology 121:1, 0505-0506). Their CAM-based system for investigating wound healing employed a method of interposition grafting where 3 mm punch biopsies of human skin were interposed gently in between the inner egg shell membrane and CAM of 7 day old chick embryo. Because human skin is interposed between the inner egg membrane and the CAM, there is no direct contact between the skin and the ambient atmosphere. Roux et al 2003A do not suggest the use of the CAM system to investigate wound healing in conjunction with topically applied factors, and indeed the lack of an epidermis-air interface could preclude such studies. There is no disclosure of any application other than wound healing studies in mechanically traumatized skin.

Transplantation of heterologous cells and tissues to the embryonic chick and, particularly, to the chorioallantoic membrane (CAM) is also being used to evaluate angiogenesis in human solid tumor growth and anti-neoplastic drug screening (see, for example, U.S. Pat. No. 6,228,345). The chick model system reproduces many of the characteristics of tumors in vivo, such as tumor mass formation, angiogenesis and metastasis. Only a few studies of human leukemia/lymphomas using this convenient system have been described, although none investigated whether engraftment to the hematopoetic system of the embryo took place. Longenecker, et al. (1977, J. Nat.l Cancer Inst. 58(4): 853-62), for example, examined whether human leukemic cells carry oncogenic viruses that attack the chicken, and not their engraftment and spread into the hematopoietic system.

Currently, the best in-vivo models for study of blood malignancy (and hematopoesis) are highly immune-deficient mice or fetal sheep and dogs (Cashman et al., 1997, *Blood* 89: 4307-4316; Zanjani, et al., 1992, Bone Marrow Transplant. 9 Suppl 1:86-9; Lutzko et al., Exp Hematol. 2002(7): 801-8). The fetal sheep or dog models are not practical for studying the biology of blood malignancies or for drug screening, because of the extremely high cost in money and space for the experiments. By contrast, NOD-SCID mice have been used extensively to study human blood malignancies. Large doses ($5 \times 10^7$) of leukemia cells from patients are required for engraftment to irradiated NOD/SCID mice, and substantial engraftment takes six weeks to over two months (Dazzi et al., 2000, *Hematol. J.* 1: 307-315). When cells are grafted directly to the bone marrow (BM), a more technically demanding procedure with lower rates of survival, they engraft in 28 to 42 days, and human cells also home to in spleen in most mice (Yahata et al., 2003 Blood 101: 2905-2913). A more immune-deficient mouse model has been described in which homozygous disruption of the $\beta 2$ microglobulin gene has been backcrossed onto the NOD/SCID background. These mice have higher levels of engraftment but are susceptible to spontaneous thymoma at an early age (6 months), reducing their value as a model for engraftment and drug testing for blood malignancies (Christianson et al., 1997, J. Immunol. 158: 3578-3586).

There exists a need for developing animal models for examining biological processes and screening drugs and therapeutic modalities on mammalian organs or tissues. Specifically, it would be highly advantageous to have a model system for large scale testing of biological processes related to mammalian cells and tissues affording physiological features such as immune cells and vasculature containing erythrocytes, while being readily accessible to manipulation and observation.

SUMMARY OF THE INVENTION

The present invention provides novel chimeric systems and screening methods utilizing mammalian grafts transplanted into avian embryos. It is now disclosed that chimeric avian embryos comprising diseased mammalian cells or tissues serve as a convenient, efficient system for screening therapeutic drugs or treatments. It is further disclosed that the chimeric avian embryos comprising normal or aberrant mammalian tissues provide a convenient and efficient system for screening potential disease causing agents, to establish their safety or lack thereof. It is yet further disclosed that the chimeric avian embryos comprising genetically altered normal or aberrant tissues may be used to screen genetic susceptibility to or methods of treatment of diseases and disorders.

Specific exemplary novel applications include intact mammalian skin explants grafted on the chorioallantoic membrane (CAM) of a fertilized avian egg for screening dermatological treatments or susceptibilities and novel systems for screening anti-cancer drugs useful for hematopoietic malignancies.

The present invention is based, in part, on histological and immunohistochemical evidence that explants of mammalian skin cultivated on the CAM provides an authentic ex vivo model system allowing the quantification of tissue damage and irritation. Furthermore, the invention is based, in part, on experimental evidence that the explant of mammalian skin transplanted on the CAM can express gene products encoded by an exogenous oligonucleotide delivered via a viral vector. The present invention further demonstrates, for the first time, that exogenous GFP-expressing mammalian cells may be incorporated in explants of mammalian skin cultivated on the CAM, and thus may provide a novel model system for examining stem cell potency.

The present invention is also based, in part, on experiments demonstrating for the first time the engraftment of mammalian hematopoietic cells, specifically malignant cells, in various organs of avian embryos, and provides rapid, cost-effective and simple methods suitable for large-scale in vivo screening of anti-cancer drugs.

In one aspect, the present invention relates to mammalian-avian chimeric systems comprising a viable fertilized avian egg and at least one abnormal viable mammalian cell population selected from the group consisting of:
  a) a skin explant comprising a population of cells, wherein at least a portion of the population of cells is transformed with at least one exogenous nucleic acid sequence;
  b) a skin explant obtained from skin having a pathological condition;
  c) a skin explant comprising a population of exogenous cells; and
  d) malignant hematopoietic cells.

The model systems of the invention are useful for in vivo examination of various biological processes and in vivo screening of drugs and treatments, as will be specified hereinbelow.

According to one aspect, the present invention provides a chimeric model system for testing biological processes in mammalian skin transformed with at least one exogenous nucleic acid sequence. This model system comprises:
  a) an explant of mammalian skin, the explant comprising a population of cells, wherein at least a portion of the population of cells is transformed with at least one exogenous nucleic acid sequence;
  b) a fertilized avian egg within an egg shell, wherein a portion of the egg shell is removed creating an aperture, wherein the explant of skin is in contact with the chorioallantoic membrane (CAM) of the fertilized avian egg such that vasculature extends from said fertilized avian egg to said explant; and optionally
  c) means for resealing the egg thereby segregating said explant from the environment outside of said egg shell.

In certain embodiments, the skin explants used in the chimeric avian-mammalian systems of the invention are of a certain minimum size. In one embodiment, the explant is at least 20 square mm, more preferably at least 25 square mm, and up to 200 square mm for chicken eggs. The size of the explant may vary for eggs of birds of other species (i.e. larger for turkey or ostrich eggs and smaller for quail eggs).

In one preferred embodiment, the mammalian skin is human skin.

The means for segregating the piece of mammalian skin serves to preserve sterility and isolate the cultured skin explant from microbes in the ambient atmosphere. In one embodiment, the means for segregating the piece of mammalian skin is fastened to the egg shell. In various embodiments, this seal is adhesive tape, plastic wrap, microscope cover glass fixed with wax, or a detached piece of the egg shell refastened to the egg shell.

Genetically transformed skin cells comprise exogenous nucleic acid sequences encoding at least one of the following: regulatory sequences or elements, gene products, functional RNA molecules, recombinant peptides and proteins, wherein the peptides and proteins may undergo glycosylation or other post-translational modifications. The skin cells may be transformed before or after the explant is transplanted onto the CAM.

Transformed skin cells may be so obtained using a variety of techniques well known in the art. In various embodiments, cells are transformed by a recombinant construct carrying the exogenous nucleic acid sequences. Different recombinant constructs include, but are not limited to viral vectors and plasmids. Transformation may be accomplished with transgenic vesicles such as liposomes containing at least one nucleic acid sequence or with naked nucleic acid molecules. In certain embodiments, the population of cells expresses the recombinant gene product for at least 5 days.

In one preferred embodiment, the skin cells are transformed with a viral vector. The viral vector may be selected from a group including, but not limited to, recombinant lentivirus, recombinant adenovirus, recombinant adeno-associated virus, recombinant papilloma virus, recombinant retrovirus, recombinant cytomegalovirus and recombinant simian virus.

The system thus provides an efficient cost-effective means for screening various putative gene therapy techniques, and to test the consequences of introducing various exogenous genes into skin tissue. The system is thus useful for screening putative skin cell targets, nucleic acid site targets, exogenous oligonucleotides, and transformation techniques.

For example, in various embodiments, the exogenous nucleic acid sequence may have a positive effect on tissue generation, hair growth or regeneration of wounded tissue in the context of wound healing. According to one embodiment, the rate of hair growth in skin explants transplanted onto the CAM can be enhanced by inducing constitutive expression of β-catenin by cells of the explant. In one embodiment, the exogenous nucleic acid sequence is a nucleic acid sequence that has a positive effect on the progression of hair generation. In one embodiment, the exogenous nucleotide encodes β-catenin.

One application which is of particular importance is the use of gene therapy to improve wound healing. In yet another embodiment, the exogenous nucleic acid sequence is a nucleic acid sequence that has a positive effect on the regeneration of damaged tissues. In various embodiments, the exogenous nucleic acid sequence may encode for a gene product selected from the group consisting of growth factors, cytokines, therapeutic proteins, hormones, fragments of peptide hormones, cytokine inhibitors, peptidic growth factors, and peptidic differentiation factors.

Gene therapy has been proposed as an advanced therapeutic technique for curing skin having a pathological condition. The current invention provides a model system for cultivating skin explants obtained from skin having a pathological condition. Examples of pathological conditions include but are not limited to psoriasis, epidermolysis bullosa, bullous pemphigoid, xeroderma pigmentosum, alopecia, seborrheic keratosis, fibrosis, restenosis, wart infection, acne, chapping, tautness, and photoaging. In one embodiment, the exogenous nucleic acid sequence has an ameliorative influence on the pathological condition.

In another embodiment, at least a portion of the explant may be exposed to at least one external modulator. External modulators include, but are not limited to, chemical agents, biological agents, contact sensitizers, allergens, topical creams, gaseous agents, pharmaceutical compositions, radiation, gaseous agents, and mechanical and thermal ablation.

According to another aspect, the present invention provides a chimeric model system for testing biological processes in diseased or abnormal mammalian skin. This model system comprises:
  a) an explant of mammalian skin, the explant comprising a population of cells, the explant is obtained from skin having a pathological condition;
  b) a fertilized avian egg within an egg shell, wherein a portion of the egg shell is removed creating an aperture, wherein the explant of skin is in contact with the chorioallantoic membrane (CAM) of the fertilized avian egg such that vasculature extends from said fertilized avian egg to said explant; and optionally
  c) means for resealing the egg thereby segregating said explant from the environment outside of said egg shell.

In various embodiments, the system is useful for studying pathological processes in abnormal or diseased skin, and screening external modulators that purportedly have an ameliorative affect on the abnormal or diseased condition.

Examples of pathological conditions include but are not limited to psoriasis, cancer, melanomas, squamous carcinomas, basal cell carcinomas, epidermolysis bullosa, bullous pemphigoid, xeroderma pigmentosum, seborrheic keratosis, fibrosis, restenosis, wart infection and acne. Other pathological or abnormal conditions include, but are not limited to, alopecia, chapping, tautness, and photoaging. Signs of photoaging are to be selected from the group consisting of wrinkles, lines, sagging, freckles, discoloration, hyperpigmentation, age spots, thinning of the skin, epidermal hyperplasia, skin elastosis, degradation of the extracellular matrix, and precancerous growths and cancer susceptibility. In certain embodiments, the pathological condition is cancer susceptibility and the skin is susceptible to cancer selected from the group consisting of melanomas, squamous and basal cell carcinomas.

In one preferred embodiment, the mammalian skin is human skin.

In another embodiment, at least a portion of the explant may be exposed to at least one external modulator, as specified above.

In another embodiment, at least a portion of the population of cells is transformed with at least one exogenous nucleic acid sequence.

In another embodiment, the exogenous nucleic acid sequence has an ameliorative influence on said pathological condition.

According to another aspect, the present invention provides a chimeric model system for testing biological processes involving intact mammalian skin in the presence of exogenous cells. This system comprises:
  a) an explant of mammalian skin, the explant comprising a population of skin cells;

b) a fertilized avian egg within an egg shell, wherein a portion of the egg shell is removed creating an aperture, wherein the explant of skin is in contact with the chorioallantoic membrane (CAM) of the fertilized avian egg such that vasculature extends from said fertilized avian egg to said explant; and optionally c) means for resealing the egg thereby segregating said explant from the environment outside of said egg shell, wherein at least one exogenous cell has been introduced into the explant.

This system is useful, for example, for determining stem cell potency by measuring teratoma formation in the skin explant grafted on the CAM. Other uses for this system include, but are not limited to, examining pathogen infection in mammalian skin, determining the metastatic ability of cancer cells, and determining the roles of different normal or genetically modified cells in wound healing.

In one preferred embodiment, the mammalian skin is human skin.

In various embodiments, the exogenous cells (i.e. cells artificially introduced into the skin explant) may be mammalian cells or non-mammalian cells. In the event that non-mammalian cells are introduced to the system, possible cell types include infectious microbes, such as fungi or bacteria or eukaryotic parasites.

In various embodiments, the exogenous cells may be introduced into the explant by topically applying them to the skin explant, by injecting them into the skin explant or by injecting them either into skin vasculature or into egg vasculature.

In one particular embodiment, the exogenous cells are stem cells. Possible types of stem cells include, but are not limited to, cord blood cells, peripheral blood cells, bone marrow cells, dermal cells, epidermal cells, neural cells, embryonic stem cells, and fat stem cells.

In yet another embodiment, the exogenous cells are cancer cells. Growth of cancer cells in the grafted skin could be used for study of subsequently applied anti-cancer agents, metastases of the tumor cells to the chick embryo, changes in normal tissue cells induced by the presence of the cancer cells and the growth of human cancer cells in a human environment.

In one embodiment, said stem cell can be distinguished from said skin explant by the presence of a genetic marker. In certain embodiments, for example when both the explant and the skin are derived from the same species, the explant may be obtained from a female and the exogenous cell obtained from a male (or alternatively, the explant is obtained from a male and said exogenous cell is obtained from a female), and may thus be distinguished by a detectable genetic marker of a sex chromosome.

In certain embodiments, at least a portion of the population of skin cells is transformed with at least one exogenous nucleic acid sequence. In certain embodiments, at least a portion of the exogenous cells expresses at least one recombinant gene product.

In other embodiments, at least a portion of the exogenous cells has been marked with a fluorescent dye.

In other embodiments, at least one biomarker of said exogenous cells has been labeled.

According to certain embodiments, the present invention relates to a chimeric system for cultivating mammalian skin explants on the chorioallantoic membrane (CAM) of a fertilized avian egg, where at least the majority of the egg shell has been removed from the fertilized avian egg. This system comprises:

a) an explant of mammalian skin, the explant comprising a population of cells;

b) a fertilized avian egg, wherein at least the majority of the egg shell has been removed from the fertilized avian egg, wherein the explant of skin is in contact with the chorioallantoic membrane (CAM) of the fertilized avian egg such that vasculature extends from said fertilized avian egg to said explant;

c) a sterilized receptacle capable of holding the fertilized avian egg; and optionally d) means for resealing the egg thereby segregating said explant from the outside environment.

In one embodiment, the entire egg shell has been removed from the fertilized avian egg.

In the event that the majority of the egg shell has been removed, the invention provides a number of advantages. For instance, in various embodiments, the lack of an egg-shell, or near lack of an egg-shell allows for easier viewing, monitoring and photographing of the embryo of the fertilized egg. Furthermore, in various embodiments there is greater access to the blood and allantoic waste of the fertilized egg, and it is possible to inject chemical or biological agents or to obtain blood or waste samples.

According to another aspect, the current invention provides a method for studying and screening various physiological and pathological processes and responses in normal and abnormal mammalian skin.

Examples of such processes include, but are not limited to, dermatological response to external modulators comprising chemical agents, biological agents, contact sensitizers, allergens, topical creams, pharmaceutical compositions, radiation, gaseous agents and mechanical and thermal ablation.

The method includes:
a) incubating a fertilized avian egg;
b) removing at least part of the egg shell of the fertilized avian egg, thereby exposing at least part of the chorioallantoic membrane (CAM) of said fertilized egg;
c) optionally placing said fertilized egg in a sterilized receptacle;
d) placing an explant of mammalian skin in contact with the CAM of said fertilized egg, at least part of the explant in contact with the ambient atmosphere, said explant comprising a population of cells;
e) optionally segregating said explant from the environment outside of said egg shell;
f) further incubating said fertilized avian egg for a period of time to allow engraftment;
g) exposing at least a portion of the engrafted explant to at least one external modulator; and
h) examining at least a portion of said explant-egg system.

In the event that the external modulator is topically administered or injected into the explant, then the exposing of step (g) will necessarily entail exposing the explant to the environment outside of the egg shell so that the external modulator may access the explant. Similarly, in various embodiments, the explant itself is examined in (h), and for these embodiments accessing the explant necessitates re-exposing the explant to the environment outside to the egg shell.

The portion of the explant may be exposed to one or more external modulators before the further incubating or after the further incubating. In various embodiments, either the explant itself is exposed to the external modulator, or the external modulator may be administered to the egg. In one embodiment, the explant-egg system is intermittently exposed to the one or more external modulators and re-incubated.

In various embodiments, the skin explant is transplanted onto the CAM of the fertilized avian egg at least 4 days post fertilization. Furthermore, in various embodiments, the incubation process disclosed in step (f) is for two to three days.

The optional segregating of step (e) serves to sterilely isolate the cultured skin explant from microbes in the ambient atmosphere. In one embodiment, the means for segregating the piece of mammalian skin is fastened to the egg shell. In various embodiments, this seal is adhesive tape, plastic wrap, microscope cover glass fixed with wax, or a detached piece of the egg shell refastened to the egg shell.

In certain embodiments, at least a portion of the explant or the fertilized egg is examined by histological, biochemical, molecular and cell biological means. In various embodiments, the skin explant itself may be examined, a blood sample may be extracted from the explant or egg vasculature and examined, various organs of the embryo may be examined, including but not limited to the spleen, liver and bone marrow of the embryo, or samples of waste obtained from the allantois are examined.

According to various embodiments, external modulators may include chemical agents, biological agents, radiation, mechanical aggression, thermal stress, gaseous agents and mechanical barriers. At least one portion of the skin explant may be exposed to one or more external modulators either before being placed on the CAM, after being placed on the CAM, or both.

The external modulators may be topically administered to the explant, injected directly into the explant, or injected into blood vessels of the fertilized avian egg.

In the event that the external modulator is a chemical agent, the invention provides a model system for screening the irritation potential, the sensitizing potential, the toxic effects or therapeutic effects of the chemical agent, or its absorption by the skin explant.

Chemical agents may include, but are not limited to, organic molecules, inorganic compounds, elements, drugs, pharmaceutical compositions, cosmetic formulations, putative irritants, sensitizers and allergens.

According to one particular embodiment, the biological agent is an infectious microbe. Examples of infectious microbes include viruses (e.g. herpes), fungi (e.g. *tinea pedis*), yeast, bacteria (e.g. *staphloccous*) and eukaryotic parasites (e.g. *leishmania*). The present invention provides a model system for studying physiological response to infectious microbes, and for treatment of such infections.

According to certain embodiments, the skin explant is exposed to an infectious microbe as well as an antimicrobial pharmaceutical. The order of the exposure can be microbe then pharmaceutical for screening post-facto treatment, or pharmaceutical then microbe for testing potential of protection from infection. In these embodiments, the invention provides a model system for screening the therapeutic and/or prophylactic effects of the pharmaceutical.

In other embodiments, the biological agents include, but are not limited to, hormones (e.g. estrogens), peptides, cytokines, chemokines, interferon formulations, nucleic acids, proteins, carbohydrates, carotenoids, lipids, fatty acids, prions, enzymes, lectins and antibodies.

In other embodiments, the biological agents are mammalian cells such as stem cells or cancer cells. In one particular embodiment, normal or genetically modified embryonic, fetal or adult stem cells are injected into vasculature of the egg, and the skin is examined after 2 to 5 days to investigate incorporation of stem cells into the skin tissue. In other various embodiments, the transport and incorporation of intravascularly injected cancer cells may be investigated. In yet further embodiments, the stem or cancer are injected or applied directly into the mammalian skin, either preceding or after grafting. In other embodiments, the stem cells are examined for their ability to form teratomas on the mammalian skin graft.

In another embodiment, the invention provides a method for examining an immune response in a mammalian skin. This method may be used to screen for modulators capable of enhancing, or, in other embodiments, inhibiting, the activation and/or mobilization of Langerhans cells (LC) present in a skin explant transplanted onto a CAM. The screened modulators may be, for example, antigens (e.g. allergens and tumor-associated antigens), contact sensitizers, and other chemical and biological agents as described above.

LC mobilization may be determined, for example, by detecting the presence of LC in different parts of the explant-egg system, e.g. the epidermis and dermis of the explant and the spleen or other immune-related tissues of the chick embryo. In other particular embodiments, LC activation is examined using, e.g., immunohistochemical methods wherein different parts of the explant-egg system are stained for LC activation markers or secreted factors associated with LC activation.

The present invention also provides a model system for studying the influence of electromagnetic radiation, including, but not limited to, UV light, on skin. In one embodiment, the UV light is administered in conjunction with a second external modulator that putatively prevents skin damage from UV light, such as a sunscreen or a piece of fabric interposing between the explant and the source of UV light. In this embodiment, the invention provides a method of screening agents which may prevent UV light induced skin damage.

In the event that the external modulator is UV light, the skin explant may be from chronically sun exposed skin as well as non-chronically sun-exposed skin.

Other types of radiation may include, but are not limited to visible light of a single or multiple wavelengths, gamma radiation, alpha radiation, beta radiation, an electromagnetic field, radiation with a frequency in the range of 100-1000 MHz, microwave, and any other type of radiation encountered by humans.

In other embodiments, at least a portion of the population of skin cells is transformed with at least one exogenous nucleic acid sequence.

In one preferred embodiment, the period of time that the skin explant is cultivated on the ectodermal surface of the CAM is at least 2 days. In another preferred embodiment, the skin explant is cultivated for at least 3 days, preferably at least 4 days, and more preferably at least 5 days on the ectodermal surface of the chicken CAM.

In one preferred embodiment, the epidermis of the CAM is lightly abraded before the explant is placed on the CAM. Examples of devices for abrading the CAM include acetone extracted and sterilized lens tissue and a sterilized fire-polished glass rod.

In another embodiment, the explant is obtained from skin having a pathological condition as previously specified.

In certain currently preferred embodiments, at least a portion of the skin explants is examined using histological and immunochemical techniques known in the art. These techniques allow for the scrutinization of skin architecture and for the proportions of and proliferation rate of various cell populations in the skin to be monitored. In one embodiment, the cell proliferation rate is estimated by measuring the rate of 3H thymidine incorporation, or bromodeoxyuridine incorporation or Ki67 or PCNA expression etc. In other embodiments, at least a portion of the explant is examined using molecular biology methods and/or biochemical methods well known in the art, e.g. western blotting, reverse-transcription polymerase chain reaction (RT-PCR), etc.

In various embodiments, the immunochemical techniques include but are not limited to immunostaining portions of the explant for biomarkers. Possible biomarkers include Ki67, thymine dimers, proliferating cell nuclear antigen, keratins, cytokines, cytokine receptors, integrin receptors, integrin receptor ligands, growth factors, melanin, immune cells, human endothelial cells, collagen, elastin, fat depositions and incorporated exogenous bromodeoxyuridine. In various embodiments, the possible biomarkers are markers of transformed cells or activated immune cells, and such as p53, specific keratins, unusual integrins, CD83 and adhesion molecules.

The current invention also provides a method for ascertaining the irritability potential and toxicity of external modulators. This may be accomplished using histological as well as immunochemical techniques. For example, histological techniques may be used to determine if skin tissue has undergone a hyperplastic response characterized by multiple additional layers of the spinous and granular layers of the skin. Immunostaining for specific markers allows for the determination of cell proliferation rate of subpopulations of cells. Biochemical and molecular biology methods such as western blotting and RT-PCR can also be used for the assay of changes in molecules associated with irritation.

In other embodiments, a chemical is applied topically to the skin, and samples of blood or urine are taken at set time intervals of hours or days, for example via a cannula. The blood or urine is assayed by HPLC or any chemical analysis for the chemical or its metabolites, by methods well known in the art.

In another aspect, the invention presents a chimeric animal model for testing drugs for chemotherapy and/or anti-cancer therapy. The animal model described in the invention is for testing chemotherapeutic or other anti-cancer drugs aimed at any one of post-relapse treatment and drug-resistant blood or stem cell derived malignancies.

The system comprises:
a) a fertilized avian egg within an egg shell, wherein a portion of the egg shell is removed creating an aperture;
b) a mammalian graft comprising a population of malignant hematopoietic cells; and optionally
c) means for resealing the egg thereby segregating said graft from the environment outside of said egg shell.

In various embodiments, the population of hematopoietic cells includes, but is not limited to, leukemic or malignant blood or stem cells. In a preferred embodiment, the graft comprises a population of human hematopoietic cells.

In one embodiment, the mammalian graft of (b) has formed at least one solid tumor in the avian embryo.

In one preferred embodiment, at least a portion of the population of cells is transformed with at least one exogenous nucleic acid sequence.

Delivery of the mammalian hematopoietic cells to the avian embryo may be effected through a variety of methods. In certain preferable embodiments, the hematopoietic cells are delivered in a manner selected from:
a) injection into the amniotic sac;
b) injection into the yolk sac;
c) intravenous injection into the chorioallantoic blood vessels; and
d) layering the cells on the chorioallantoic membrane.

In other embodiments, the mammalian graft further comprises a second population of stromal cells. The stromal cell population may be co-engrafted into the avian embryo with the hematopoietic graft, or engrafted into the avian embryo prior to or after transplanting the hematopoietic graft.

In certain preferred embodiments, the stromal cell population and the hematopoietic cell population are taken from different mammalian species (e.g. human hematopoietic graft and murine stromal graft).

In other embodiments, preferred avian embryos include, but are not limited to: chick embryos (*Gallus gallus*), turkey embryos (*Meleagris gallopavo*) and duck embryos (*Anas platyrhyncha*).

In another aspect, the present invention provides a method for screening anti-cancer drugs, comprising:
a) engrafting a population of malignant mammalian hematopoietic cells into an avian embryo;
b) exposing the hematopoietic cells to at least one test drug; and
c) analyzing the population of engrafted cells after a determined period of time.

In one embodiment, the method further includes prior to step (b) a step of assaying for the presence of mammalian cells in the embryo after a pre-determined period of incubation.

In certain embodiments, successful drug candidates will reduce at least 50%, preferably at least 70%, and more preferably at least 90% or more of the engrafted cells. In other embodiments, successful drug candidates will lead to terminal differentiation/cessation of malignancy of the engrafted cells.

In a preferred embodiment, the graft comprises a population of human hematopoietic cells. In another embodiment, the human hematopoietic cells are obtained from a subject in need thereof, i.e. a subject having a hematopoietic neoplastic disorder, and thus the invention provides a rapid and efficient means of determining the most effective drug for the individual subject in need thereof.

In one embodiment, said pre-determined period of incubation may be between 1 and 30 days of incubation. The optimal period of incubation varies according to the type of malignant cell inoculated as well as to the location and method of grafting the cells.

In another embodiment, at least a portion of the cell population is transformed with at least one nucleic acid sequence. In a preferable embodiment, at least a portion of the cells express GFP or another reporter gene product, allowing an easy means of detecting engraftment.

According to currently preferred embodiments, the hematopoietic cell population is delivered to the avian embryo as described above.

In other embodiments, the method further comprises prior to step a) a step of treating a population of malignant hematopoietic cells with an array of test drugs, for a determined period, in vitro, and evaluating which drugs were effective in killing said cells, whereby the drugs which were able to effectively reduce the number of cells by at least 20% preferably at least 50% and more preferably at least 70% may be pursued onto the next step, in vivo.

In various embodiments, the drug can be administered to the malignant cells before or after transplantation at one or various time points. The drug can be administered alone, after or in combination with other anti neoplastic agents or pro engraftment agents, or agents which cause changes in chromatin structure, methyltaion or acetylation of DNA.

The drug can be administered to animals before or after grafting of the malignant hematopoietic cells at one or various time points. The grafted embryos may be pretreated with irradiation, changes in oxygen or temperature, chemokines, cytokines, DNA altering drugs or antibodies prior to the grafting of malignant cells.

These and other embodiments of the present invention will become apparent in conjunction with the figures, description and claims that follow.

BRIEF DESCRIPTION OF THE DRAWINGS

FIG. 6 illustrates overexpression of β-catenin in intact mouse skin resulting in extensive hair follicle growth (marked with arrows).

FIG. 8 contains a micrograph demonstrating staining of Langerhans cells (LC) with antibodies against CD1a.

FIG. 11 shows human skin with a puncture wound grafted on the chicken CAM for 7 days that received an intradermal injection of human embryonic stem cells expressing GFP 5 days previously.

DETAILED DESCRIPTION OF THE INVENTION

Figure 1:
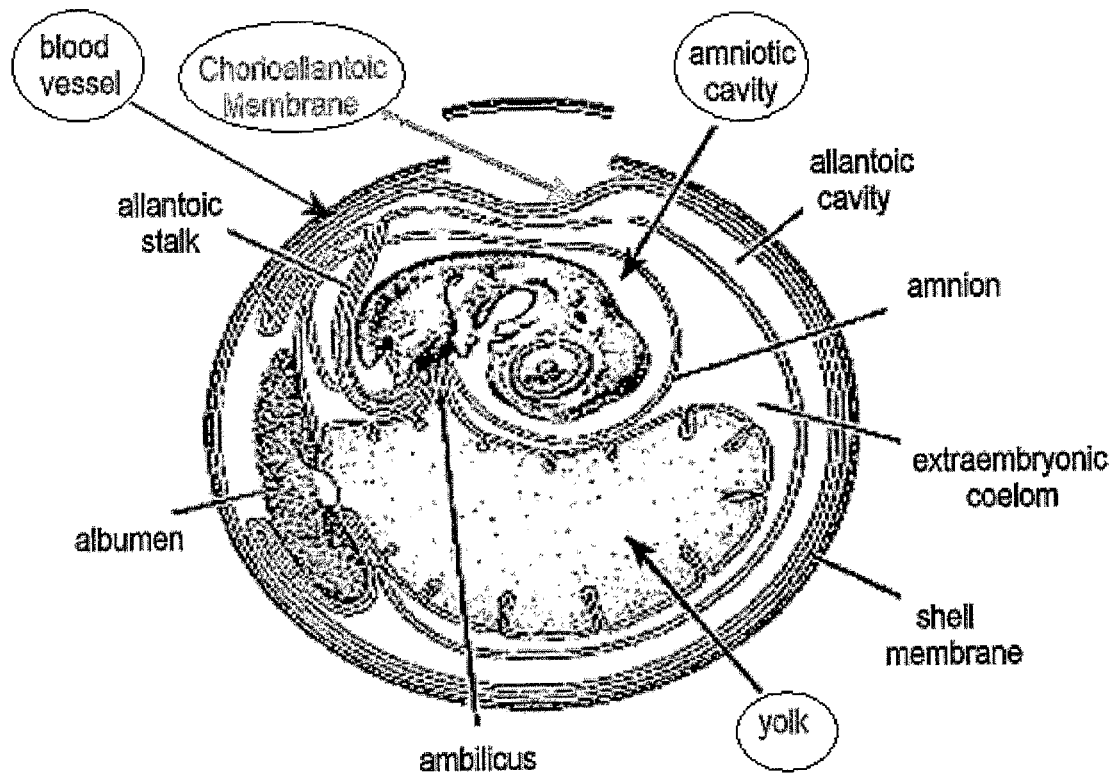
FIG. 1 is a schematic representation of a fertilized chicken egg.

The present invention relates to animal model systems comprising a chimera between an avian embryo and a mammalian organism. Chimeric model systems comprising normal, diseased or genetically transformed mammalian cells and tissues transplanted into avian embryos, and uses thereof for in vivo testing of drugs and therapeutic modalities are disclosed.

Specific exemplary novel applications include intact mammalian skin explants grafted on the chorioallantoic membrane (CAM) of a fertilized avian egg for screening dermatological treatments or susceptibilities and novel systems for screening anti-cancer drugs for hematopoietic malignancies, as will be described in detail hereinbelow.

1. DEFINITIONS AND TERMINOLOGY

The phrase "candidate compound" or "candidate agent" as used herein refers to an agent which is tested or to be tested for a defined activity on the skin explant and/or the egg-explant system. Such activity may be, without limitation, proliferative, wound-healing, irritative, toxic, anti-proliferative, carcinogenic, wrinkle-smoothing, anti-cancer, differentiating, anti-differentiating, immuno-modulating or anti-microbial activity. Such agents may include, but are not limited to, chemical and biological agents, radiation and mechanical or thermal ablation.

The term "skin" refers to the all body surfaces that are in contact with the outside world. Thus, "skin" refers to outer protective covering of the body, consisting of the corium and the epidermis, and is understood to include sweat and sebaceous glands, hair follicle structures as well as hair. Moreover, the term "skin" is also understood to also include all external mucous body surfaces such as oral, nasal conjunctival, vaginal and anal. Throughout the present application, the adjective "cutaneous" may be used, and should be understood to refer generally to attributes of the skin, as appropriate to the context in which they are used.

The term "skin explant" as used herein is directed to a skin tissue obtained from a mammal, comprising a tissue retaining the epidermis, dermis, and basal lamina, their vasculature and cutaneous structures such as, but not limited to, sweat and sebaceous glands, hair follicle structures and hair. The skin explant may optionally include the underlying or "subcutaneous" fat.

The "corium" or "dermis" refers to the layer of the skin beneath deep to the epidermis, consisting of a dense bed of vascular connective tissue, and containing the nerves and terminal organs of sensation. The hair roots, and sebaceous and sweat glands are structures of the epidermis which are deeply embedded in the dermis.

The term "exogenous nucleic acid sequence" indicates that the nucleic acid molecule is from a source other than the target cell, into which the nucleic acid molecule is to be introduced. It should be recognized, however, that the exogenous nucleic acid molecule also can be from other cells of the same type as the target cells.

An "exogenous cell", in the context of the present invention, is a cell artificially introduced into a host organism, organ or tissue. Exogenous cells may also be taken from the same tissue/organ as the target tissue/organ to which they are introduced.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides that may optionally include intron sequences that are derived from chromosomal DNA. The term "intron" refers to a DNA sequence present in a given gene that is not present in the mature RNA and is generally found between exons.

The phrase "gene product" refers to proteins, peptides and functional RNA molecules. Generally, the gene product encoded by the nucleic acid molecule is the desired gene product to be supplied to a subject. Examples of such gene products include, but are not limited to, proteins, peptides, glycoproteins and lipoproteins normally produced by an organ of the recipient subject.

The term "gland" refers to an aggregation of cells specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface. The ordinary or eccrinesweat glands are distributed over most of the body surface, and promote cooling by evaporation of the secretion; the apocrine sweat glands empty into the upper portion of a hair follicle instead of directly onto the skin, and are found only in certain body areas, as around the anus and in the axilla.

The term "hair" (or "pilus") refers to a threadlike structure, especially the specialized epidermal structure composed of keratin and developing from a papilla sunk in the corium, produced only by mammals and characteristic of that group of animals. The term also refers to the aggregate of such hairs. A "hair follicle" refers to one of the tubular-invaginations of the epidermis enclosing the hairs, and from which the hairs grow; and "hair follicle epithelial cells" refers to epithelial cells which are surrounded by the dermis in the hair follicle, e.g., stem cells, outer root sheath cells, matrix cells, and inner root sheath cells. Such cells may be normal non-malignant cells, or transformed/immortalized cells.

A "gene with a positive effect" on the regeneration of the damaged or defective tissue includes all DNA sequences which have a promoting effect on regeneration when translated as a protein or polypeptide, but also, for example, as an antisense molecule, a ribozyme or a small interfering RNA (siRNA).

As used herein, "proliferating" and "proliferation" refer to cells undergoing mitosis.

The terms "transformation" or "transform" refers to any genetic modification of cells and includes both transfection and transduction, as specified in detail below. A cell may be transformed with a nucleic acid sequence which is partially or entirely heterologous, i.e., foreign, to the cell in which it has been inserted or introduced, or with a nucleic acid which is homologous to an endogenous gene of the cell has been inserted. In the latter case, however, the homologous nucleic acid is designed to be inserted, or is inserted, into the cell's genome in such a way as to alter the genome of the cell into which it is inserted. For example, the homologous nucleic acid is inserted at a location which differs from that of the natural gene or the insertion of the homologous nucleic acid results in a knockout of a particular phenotype. The nucleic acid inserted into the cells can include one or more transcriptional regulatory sequences and any other nucleic acid, such as an intron, that may be necessary for optimal expression of a selected nucleic acid.

The term "hematopoietic cell" refers to any type of cell of the hematopoietic system, including, but not limited to, undifferentiated cells such as hematopoietic stem cells and progenitor cells, and differentiated cells such as megakaryocytes, erythrocytes, leukocytes, granulocytes, monocytes, lymphocytes and natural killer cells. The term "hematopoietic malignant cell" comprises both hyperplastic/neoplastic cells of hematopoietic origin isolated from a mammal and hematopoietic cell lines (e.g. leukemic cell lines such as K562).

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia and the myeloproliferative diseases (MPD) polycythemia vera (PV) and essential thrombcythemia (ET). Additional exemplary myeloid disorders include, but are not limited to, acute promyeloid leukemia (APML), acute myelogenous leukemia (AML) and chronic myelogenous leukemia (CML); and myelodysplastic syndrome (MDS), lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM), myeloma and plasmacytoma and plasma cell leukemia Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

2. EXPERIMENTAL TECHNIQUES

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higginis eds. 1984); Transcription And Translation (B. D. Hames & S. J. Higgins eds. 1984); Culture of Animal Cells (R. I. Freshney, Alan R. Liss, Inc., N.Y. 1998); Gene Transfer Vectors for Mammalian Cells (J. H. Miller and M. P. Calos eds., 1987, Cold Spring Harbor Laboratory); Methods in Enzymology, Vols. 154 and 155 (Wu et al. eds), Immunochemical Methods In Cell And Molecular Biology (Mayer and Walker, eds., Academic Press, London, 1987); The Science of Laboratory Diagnosis (John Crocker and David Burnett, Isis Medical Media Oxford, 1998); Using Antibodies: A Laboratory Manual Portable Protocol No. I (Edward Harlow, David Lane, and Ed Harlow, 1998); and Handbook of Experimental Immunology, Volumes I-IV (D. M. Weir and C. C. Blackwell, eds., 1986).

3. TESTING CUTANEOUS BIOLOGICAL PROCESSES USING THE CAM MODEL SYSTEM

Exemplary applications for the cultivation of skin explants on the chorioallantoic membrane of a fertilized egg include, but are not limited to:
(a) identification and elucidation of physiological and biochemical processes involved in normal homeostasis of the skin;
(b) studying the effect on the normal homeostasis of skin with respect to changes in the environment including changes in nutrients and the presence of potentially toxic agents;
(c) understanding the pathway of changes in skin that are triggered at the beginning and during pathogenesis or trauma;
(d) identification of repair mechanisms that reverse the adverse effects in an altered environment associated with pathogenesis or trauma.
(e) as a skin equivalent for drug screening and cytotoxicity studies.
(f) for investigating metastasis by injecting cancer cells into the grafted skin or into the avian embryo's vasculature.
(g) examining immune responses in mammalian skin.
(h) determining stem cell potency.
(i) determining transcutaneous absorption and/or penetration and/or metabolism of a chemical.

Preferred embodiments for implementing and utilizing these chimeric systems and methods are specified in detail hereinbelow.

3.1. Cultivating Transplanted Skin Explants on the CAM of an Avian Egg.

A salient feature of the model system comprising mammalian skin explants transplanted on the ectodermal surface of the CAM of a fertilized egg is that the skin maintains in vivo like histology and morphology for a period of time that can last up to 11 to 14 days from the time the skin is transplanted onto chicken CAM. Histological examination of skin cultured in the model revealed that not only was the organization of the dermis and epidermis retained, but there was an ongoing differentiation and maturation process analogous to that found in vivo. Immunohistochemistry data confirmed these findings, and the expression of proliferation markers indicated that cultured skin cells continued to cycle.

The inventors note that the architecture of the envasculated skin explants cultivated on the CAM incorporates many physiological features associated with an in vivo system. The cultivated skin has epithelial tissue/connective tissue structure. Keratinocytes of the epidermis remain associated with the connective tissue- and the normal tissue architecture is preserved including the hair follicles. Skin cells are nourished by circulating plasma and gases are exchanged by circulating erythrocytes. It was found that hair associated with skin explants can regenerate and grow during the period skin explant is cultivated on the CAM. The cultivated skin includes a basal lamina supporting the epidermal cells, an extracellular matrix which includes the dermal cells, and at least one invagination, e.g., at least one hair follicle. The association between skin epithelial tissue and the skin connective tissue facilitates intercellular communication. Importantly, there is an epidermis-air interface.

We note that although the skin explant is vascularized with anastomosis between host and graft blood vessels, the skin explant is not in itself innervated by the host chicken's nervous system. Not wishing to be bound be any particular theory, it is likely that some nervous elements of the grafted skin remain intact such as pacinian and merkel corpuscles. In addition, immune elements are present in the grafts, derived both from the human skin (e.g. dendritic cells) and the few circulating immune cells of the chick.

The CAM-based model system of the current invention includes regenerating hair on the skin explant, something that no previous investigators using a system comprised of a skin explant placed onto the CAM have disclosed. This enables for the screening of chemical agents that color hair or induce hair generation or loss. Furthermore, the current invention provides for genetically transformed cells which expressing a gene product(s) that has an ameliorative effect on various skin traumas or disease. One additional application of the present invention is therefore to screen various gene therapy techniques related to hair generation or loss.

Other investigators have asserted (Rouse et al. 2003A) that skin grafted using a so-called technique of interposition is markedly better than skin grafted by placement on the CAM This technique of interposition entails interposing the explant between the inner egg membrane and the CAM. This technique purportedly enhanced the interaction between the grafted explant and the CAM.

As discussed below in the section entitled "Examples", results were obtained without the need for invoking the technique of interposition. Interposing the skin explant between the inner egg membrane and the CAM has the significant disadvantage that it can preclude use of the CAM system to investigate biological processes involving topically applied external modulators, and at least partially blocks the normal air-epidermal interface.

In various embodiments, the shape of the skin explant can vary. Possible shapes include circular, rectangular, triangular, as well as other shape.

Not wishing to be bound by any particular theory, it was found that larger skin explants exhibit a tendency to incorporate to the fertilized CAM at a higher success rate than smaller skin explants. In preferred embodiments, skin explants are used whose surface area is at least 20 square millimeters, more preferably at least 30 square millimeters, and most preferably at least 50 square millimeters.

The present invention is based, in part, on the experimental finding that skin explants transplanted onto the CAM of a fertilized chicken egg may be maintained for 11 to 14 days. Of course, the skin may be cultured for shorted periods of time, as short as at least two days, and this should not be construed in any way as a limitation.

It is noted that no media or blood is necessary in order to cultivate transplanted skin explants on the CAM.

In addition, it is possible to cultivate several skin grafts on a single CAM. In many circumstances, this can lower the cost of practicing the invention and make the invention more convenient to practice.

In various embodiments, the skin explant is cultivated on the CAM of avian eggs wherein the majority of the egg shell has been removed from the fertilized avian egg. In these embodiments, the fertilized is placed in a receptacle adapted for holding the fertilized egg. The skilled artisan is directed to references describing well-known protocols for incubating shell-less, fertilized avian eggs (Hamamichi and Nishigori 2001. Toxicol. Lett. 119: 95-102; Fisher, C. J. 1993. Chick Embryos in Shell-less Culture, Pages 105-115, in *Tested studies for laboratory teaching*, Volume 5 (C. A. Goldman, P. L.

Hauta, M. A. O'Donnell, S. E. Andrews, and R. van der Heiden, Editors). Proceedings of the 5$^{th}$ Workshop/Conference of the Association for Biology Laboratory Education (ABLE); Tufan et al 2004. Akdogan Esat Adiguzel Neuroanatomy, 2004, 3 8-11). None of these references disclose, or suggest, transplanting a skin explant onto the CAM of the fertilized egg.

It is noted that the portion of egg shell that has actually been removed from the fertilized egg shell is immaterial. In one particular embodiment, the entire egg shell has been removed from the fertilized avian egg.

One preferred embodiment of the invention is to use fertilized chicken eggs. Nevertheless, the invention can be practiced using any avian eggs. Thus, in different embodiments turkey, ostrich, quail, duck, pheasant, grouse, or other bird eggs may be used. It is further noted that the duck egg incubation period is 28 days longer than the chick egg incubation period, and thus the explant is maintainable a concomitant period longer when transplanted onto duck eggs as opposed to chick eggs. It is also noted that the turkey egg incubation period is 7 days longer than the chick egg incubation period, and thus the explant is maintainable a concomitant period longer when transplanted onto turkey eggs as opposed to chick eggs. In certain embodiments, subcutaneous fat is mechanically removed from the skin explant before transplanting the explant onto the CAM. In other embodiments, subcutaneous fat is retained before transplanting to the CAM, and the effect of treatments on said fat is examined.

In one preferred embodiment, the CAM is abraded prior to the transplant of the skin explant onto the ectodermal surface of the CAM to partly destroy the ectodermal epithelium of the CAM. Abrading the CAM can improve the rate at which the explants take to the CAM. In different embodiments, the CAM may be abraded with a fire-polished glass rod or with lens paper.

After the skin explant is transplanted onto the ectodermal surface of the CAM, the system is further incubated in order to allow the graft to take. During this period of time, anastomosis of the host and explant blood vessels occurs and the skin graft is nourished by the chick's plasma and gases exchanged by chick erythrocytes. During this additional incubation period, it is necessary to isolate the skin explant from microbes in the ambient atmosphere outside of the egg shell which could contaminate the incubating explant and possibly lead to tissue degradation. Possible means for isolating the skin explant (sealing the egg) include, but are not limited to, saran wrap, adhesive tape, the egg shell itself, and glass-coverslips sealed with wax.

3.2. Determining the Effect of External Modulators.

In one embodiment, at least one portion of the skin explant may be exposed to one or more external modulators either before being placed on the CAM, after being placed on the CAM, or both.

In various embodiments of the present invention, external modulators may be applied to the chimeric system, using various routes of administration. According to preferable embodiments, the modulator may be topically administered, injected directly into the explant, or injected into blood vessels of the fertilized avian egg. In one particular embodiment, the external modulators are injected into the egg blood vessels on days 11 or 12 of incubation. In one embodiment, the systemic injection is performed using a tuberculin syringe with 27-29 gauge needle. In one particular embodiment, the external modulators are injected into the egg blood vessels via an additional small window in the eggshell, using well methods well established for the injection of viruses into chick eggs for grow production of vaccines. In various embodiments, this window is formed using a dremel-type saw.

U.S. patent application 20030175328 discloses a patch for the controlled delivery of cosmetic, dermatological, and pharmaceutical active ingredients into the skin. The current invention provides a method of screening agents delivered to the skin using a patch as described in U.S. patent application 20030175328.

It is noted that the present invention relates to a model system wherein gene products such as polypeptides and proteins are directly imported into the cells of the skin explant. Furthermore, it is noted that specific importation of biologically active molecules including proteins and polypeptides into cells by linking an importation-competent signal peptide to the molecule of interest was disclosed in U.S. Pat. No. 5,807,746 as well as United States Patent publication number 20020151004. In various embodiments, the gene products are imported into the cells of the explant before transplanting onto the CAM, or alternatively after transplanting onto the CAM.

According to various embodiments, external modulators may include, but are not limited to, chemical agents, biological agents, radiation, mechanical aggression, thermal stress, contact sensitizers, allergens, gaseous agents and mechanical barriers.

Screening of Chemical Agents

In the event that the external modulator is a chemical agent, the invention provides a model system for screening the irritation potential, the sensitizing potential, the toxic effects or cosmetic or therapeutic effects of the chemical agent, and/or its ability to be absorbed by the skin explant.

Examples of chemical agents include but are not limited to surfactants, retinoids, carotenoids, food additives, moisturizers, mustard gas, organic molecules, inorganic compounds, vitamins, UV absorbing agents, UV protecting agents, perfumes, cosmetic formulations, lacquers, glues, paints, colorants, detergents, balms, creams, dyes, hair dyes, emulsions, gels, greases, shake lotions, pastes, oils, liposome formulations, lotions, mousses, ointments, suspensions, aqueous solutions, salves, solvents, shampoos, pollutants, steroids, shower gels, antibiotics, sulfa drugs, antiseptics, disinfectants, herbal formulations, anti-inflammatory agents, pharmaceutical compositions, aerosols, cleaning products, powders, petroleum jelly, anti-microbial agents, soaps, nail polish, acid rain, gasoline, kerosene, alcohols, industrial solvents, caustic chemicals, herbicides, metals, chelating agents, pesticides, mediations, fumigants, insecticides, fungicides, cleaning materials, contact sensitizers, allergens, impregnated dressings, solutions, impregnated dressings, occulative dressings, compression dressings, salves, herbal formulations, gallium compounds, solvents, kinase modulating agents, phosphate buffered saline (PBS), enzyme inhibitors, protease, petroleum jelly, secretions of plants and animals, endotoxins, antimicrobial formulations, tazarotene formulations, bexarotene formulations, azole formulations, topical antibiotic formulations (e.g. tetracycline family), plant derived toxins (e.g. poison ivy), animal-derived toxins, putative ameliorative agents (e.g. aloe vera), depilatory or hair growth-enhancing reagents and putative anti-aging formulations.

In one embodiment, skin irritation is measured by determining cell proliferation in the treated graft. A non-limitative example of quantifying human skin irritation is disclosed in Example 2 below.

In other embodiments, tissue absorption and penetration of topically administered chemicals are determined, for example by determining its presence in the different layers of the skin (e.g. by tracking fluorescent or labeled chemicals using microscopy), or its penetration through the skin and subsequent transfer to the bloodstream, by collecting blood or urine samples and assaying them, e.g. by HPLC or any chemical analysis, for the chemical or its metabolites.

Screening Biological Agents

According to one particular embodiment, the biological agent is an infectious microbe. Examples of infectious microbes include viruses (e.g. herpes), fungi (e.g. *tinea pedis*), yeast, bacteria (e.g. *staphloccous*) and eukaryotic parasites (e.g. *leishmania*). The present invention provides a model system for studying physiological response to infectious microbes, and for treatment of such infections.

According to certain embodiments, the skin explant is exposed to an infectious microbe as well as an antimicrobial pharmaceutical. The order of the exposure can be microbe then pharmaceutical for screening post-facto treatment, or pharmaceutical then microbe for testing potential of protection from infection. In these embodiments, the invention provides a model system for screening the therapeutic and/or prophylactic effects of the pharmaceutical.

In one embodiment, the invention provides a method for identifying an inhibitor of viral infection or for examining anti-viral activity of a candidate agent. In this embodiment, the infectious microbe is a virus, including, but not limited to a hepatitis virus, e.g., hepatitis B or hepatitis C, or a human papilloma virus (HPV), e.g., HPV-6, HPV-8, or HPV-33. In one particular embodiment, when infected with a virus, the explant can be used in a method for identifying an inhibitor of viral infectivity. The explant is then contacted with a candidate agent, e.g., an agent which is being tested for anti-viral activity, and the level of infectivity (e.g., viral loading, new infectivity, etc) in the presence of the candidate agent is measured and compared to the level of infectivity by the virus in the absence of the candidate agent. A decrease in the level of infectivity of the virus in the presence of the candidate agent is indicative of an inhibitor of viral infectivity. In another particular embodiment, the explant is first treated with the candidate agent and then contacted with the virus, and the level of infectivity is then determined.

In other embodiments, the biological agents include, but are not limited to, hormones (e.g. estrogens), peptides, cytokines, chemokines, interferon formulations, nucleic acids, proteins, carbohydrates, carotenoids, lipids, fatty acids, prions, enzymes, lectins and antibodies.

In other embodiments, the biological agents are mammalian cells such as stem cells or cancer cells. In one particular embodiment, normal or genetically modified embryonic, fetal or adult stem cells are injected into vasculature of the egg, and the skin is examined after 2 to 5 days to investigate incorporation of stem cells into the skin tissue. In other various embodiments, the transport and incorporation of intravascularly injected cancer cells, their effects on normal skin cells, and the effects of anti-cancer therapies may be investigated. In yet further embodiments, the stem or cancer are injected or applied directly into the mammalian skin, either preceding or after grafting. In other embodiments, the stem cells are examined for their ability to form teratomas on the mammalian skin graft.

Wound Healing

In one embodiment, the model system of skin explants cultivated on the CAM can be employed for screening agents that modulate wound healing. Repair of skin lesions is known to be a highly complex process that includes primary epithelial cell migration as well as replication of epidermal cells in response to molecular signals from underlying connective tissue. Under controlled culture conditions, factors controlling healing can be carefully monitored. Furthermore, the regenerating skin cells are nourished by circulating blood which can also serve to remove toxins from a wound site. The model system also incorporates additional physiological features such as an interface between the epidermis and the ambient atmosphere. These physiological features bestow higher clinical relevance to results obtained using the CAM based model system than systems using skin or artificial skin substitutes kept submerged in culture medium.

One parameter that can be scrutinized in order to monitor the wound healing process is the rate of cell cycling. Normal epidermis has a low mitotic activity with cells cycling every 200-300 hours. When the epidermis is wounded, a burst of mitotic activity takes place so that the cells divide up to 10 times faster depending on the conditions and severity of the wound (Pinkus H. (1951) J. Invest. Dermatol. 16:383-386) Immuncytochemical staining for proliferation markers such as PCNA, Ki67 or BrdU incorporation may be employed to characterize cell proliferation in particular cells within the skin tissue, and thus will allow for the investigation of wound healing in variety of circumstances.

Radiation

In another embodiment, the modulator is electromagnetic radiation, including, but not limited to: UV radiation, gamma radiation, alpha radiation, beta radiation, an electromagnetic field, radiation with a frequency in the range of 100-1000 MHz, microwave, and any other type of radiation encountered by humans.

Exposure of skin to UV radiation can cause diverse biological effects, including sunburn (inflammation), induction of skin cancer (melanoma), premature skin aging and alteration in cutaneous immune cells (immunosuppression) all leading to damage of the skin cells. Skin cell damage due to UV is induced by several mechanisms, such as UV-induced immunosuppression, UV-induced DNA-damage and accumulation of DNA-damage.

It is known in the art that exposure to UVB affects Langerhans cells (LC) in at least two distinct pathways. Intercellular adhesion molecules-1 (ICAM-1) and especially CD86 expression is significantly decreased. In addition, LC viability is reduced, which leads to apoptotic cell death. Both mechanisms contribute to UVB-induced immunosuppressive effects. Other markers for UV damage include, for example, altered cytokines production and secretion by keratinocytes (KC), and expression of apoptotic markers, such as increased bcl-2 expression, pyrimidine dimers and subsequent expression and accumulation of p53 proteins. The presence of these markers for UV damage may be assayed by methods well known in the art.

The current invention provides a method for studying the influence of electromagnetic radiation on mammalian skin, and provides a method for screening such candidate agents. One salient feature of the present invention is invasculation with circulating erythrocytes. Thus the present invention provides a model system for studying UV induced damage and for screening candidate agents in a physiological relevant model system with a circulating blood stream that can transport toxins away from the irradiated region.

Classical UV skin protectors which are used as sunscreens absorb UVA or UVB radiation directly on the skin surface. The protection provided is expressed by their Sun Protection Factor (SPF), which is the minimal dose at which an erythema is observed (Minimal Erythema Dose, MED) and which is highly dependent on the user's skin type. The use of such sunscreens is limited in that they only provide a certain degree of protection while being directly exposed to the sun. They have no regenerative effect, nor can they interact or prevent any UV-induced biochemical changes in the skin.

Techniques for irradiating skin with UV radiation are well known in the art (Bäckvall et al. 2002. Experimental Dermatology 11: 359-356). Irradiation sources are commercially available, and one example of such a device is the SUPUVA-SUN 3000 device (Mutzhas, Germany). These well known devices are equipped with filters allowing for the irradiation of the skin explants with UVB, UVA and near infrared irradiation. Appropriate UV doses are also well known in the art, and the skilled practitioner is once more referred to Bäckvall et al. 2002. Similarly, appropriate distances between the irradiation source and the skin explants are also well known, and the skilled practitioner is once more referred to Bäckvall et al. 2002. Thus, in order to avoid the excessive heating of the skin explant during and after irradiation, apparatuses and techniques previously discussed in the literature, for example in Bäckvall et al. 2002, are appropriate.

In the event that the skin is irradiated after transplantation, light sources such as those disclosed in Bäckvall et al. 2002, are also appropriate, but special attention must be paid to not excessively heat the fertilized egg as well. Thus, for example, a similar light source can be used with UV conducting fiber-optic light conduits. The light can be focused to a very small spot on the skin grafted to the CAM, so as to avoid the generation of large amounts of heat.

Immune Modulators

In another embodiment, the invention provides a method for examining an immune response in a mammalian skin. The epithelium of both skin and mucous membranes is richly populated with immature dendritic cells, called Langerhans cells (LC). These phagocytic leukocytes are poised for capture of antigens which may enter the epidermis through physical breaches in the stratum corneum. After physical trauma to the skin, signals are generated that induce LC to leave the epidermis and migrate into the dermis and through afferent lymphatics to lymph nodes, carrying with them any antigens which had penetrated the protective stratum corneum (i.e. viral, bacterial, parasitic, allergic). Very small, lipophilic molecules, and some highly reactive molecules known as skin sensitizing agents, such as dinitrofluorobenzene (DNFB), poison ivy catechol, oxazolone, etc., may penetrate the intact stratum corneum, subsequently binding to proteins in the underlying epidermis and activating LC.

Captured protein antigens are internalized and degraded by the LC to yield small peptides which are incorporated into the peptide binding grooves of major histocompatibility complex (MHC) molecules. The MHC-peptide complexes are then inserted into the plasma membranes for presentation to T cell receptors. During their migration to the lymph nodes, the Langerhans cells differentiate into mature dendritic cells, losing their phagocytic properties and instead, expressing high levels of MHC class I and II molecules as well as costimulatory and adhesion molecules, essential for effective antigen presentation.

In certain embodiments, the invention provides a method of screening for modulators capable of enhancing, or, in other embodiments, inhibiting, the activation and/or mobilization of Langerhans cells present in a skin explant transplanted onto a CAM. The screened modulators may be, for example, antigens (e.g. allergens and tumor-associated antigens), contact sensitizers, and other chemical and biological agents as described above, as well as electromagnetic radiation.

According to certain embodiments, the method is useful for determining the ability of a modulator to induce or enhance an immune response. For example, the method is useful for examining the side effects of pharmaceuticals and cosmetics, and for screening for immunostimulating agents useful to promote an anti-tumor response (e.g. tumor-associated antigens such as HR-gp100, described by Frankenburg et al., Immunol Lett. 2004 Jul. 15; 94(3):253-9, and derivatives thereof), among other uses. In these embodiments, the explant is exposed, before and/or after engraftment, to a modulator to be examined, and the explant-egg system is examined for LC activation and/or mobilization. In certain particular embodiments, LC mobilization is determined by detecting the presence of LC in different parts of the explant-egg system, e.g. the epidermis and the dermis of the explant, and the spleen of the chick embryo (an embryonic avian hematopoietic tissue). By means of non-limitative examples, a decrease in $CD1a^+$ cells in the epidermis indicates LC migration to the dermis or bloodstream, and a significant increase in $Langerin^+$ cells in the dermis indicates the presence of epidermal LC in the dermis. In another embodiment, the expression of chemokine receptors (e.g. CCR7) is determined, which presence indicates initiation of the homing process. In other particular embodiments, LC activation is examined using, e.g., immunohistochemical methods wherein different parts of the explant-egg system are stained for LC activation markers (e.g. CD83). In other embodiments, the explant may be assayed for secreted factors associated with LC activation or migration, including, but not limited to, matrix degrading enzymes (e.g. MMPs and elastase), ECM degradation products, cytokines and chemokines. In other embodiments, other experimental methods, including, but not limited to polymerase chain reaction (PCR) and Fluorescence-activated cell sorting (FACS), are used. For example, without limitation, a PCR reaction using human-specific primers may be used to detect human cells in the spleen, indicating homing of the LC. Several non-limitative examples for determining LC activation and mobilization are specified in detail in the Examples hereinbelow.

In other embodiments, the method is useful for screening for anti-inflammatory modulators, i.e. modulators capable of reducing or inhibiting an immune response (e.g. for the treatment of inflammatory and autoimmune diseases). In certain particular embodiments, the ability of a first modulator to inhibit an immune response induced by a second modulator is examined. In these embodiments, the explant is exposed to a second modulator (e.g. an allergen, a contact sensitizer, a chemical irritant or an infectious microbe) before, after or simultaneously with the first modulator to be examined, and LC reaction is determined as described above.

Screening Methods

The current invention is based, in part, on immunocytochemical evidence that skin explants transplanted onto the CAM exhibit an in vivo like morphology. This immunochemical evidence was, in part, obtained by immunostaining for appropriate markers in order to ascertain that cells are proliferating and for keratins to determine that the physiological layering of the epidermal cells is retained that the human blood vessels are retained in the dermis. Furthermore, it is possible to immunochemically examine cultivated skin explants in order to study biological processes associated with irritation, toxicology, aging, inflammation and wound healing.

Possible cell markers include but are not limited to caspases, involucrin, LAP-70, cathepsin D, Her2-neu, P53, S100, epithelial marker antigen (EMA), TdT, MB2, MB3, PCNA, and Ki67. Other exemplary markers which may be assayed in different embodiments of the invention include, but are not limited to, cytokines, cytokine receptors, integrin receptors, integrin receptor ligands, growth factors, melanin, immune cells, human endothelial cells, incorporated exogenous bromodeoxyuridine, specific keratins, unusual integrins, chemokine receptors, adhesion molecules, collagen, elastin, melanin and fat depositions.

Other markers for determining normal or pathological skin physiology (e.g. in aged skin and in skin of diabetic patients), include, but not limited to, markers of the following parameters: (i) connective tissue synthesis, which can be measured, for example, by staining for collagen (e.g. using MASSON trichrome stain, collagen antibodies or radioactive hydroxyproline incorporation), (ii) elasticity (measured e.g. using anti-elastin antibodies or histochemical detection of elastin with conventional methods including, but not limited to Hartls resorcin-fuchsin for staining elastic fibers as described in the Manual of Histologic Staining Methods of the Armed Forces Institute of Pathology, Third edition edited by Lee G. Luna, 1968), (iii) cell proliferation (measured e.g. with PCNA, Ki67 or BrDU antibody staining) (iv) blood vessel formation (measured e.g. using hematoxylin and eosin or CD31 immunostaining); (iv) epidermal differentiation (measured e.g. using K1/K10 or fillagrin/loricrin immunostaining); and (v) skin inflammation (observed, for example, by abscess formation and excessive leucocytosis, which may be detected e.g. by hematoxylin and eosin staining and myeloperoxidase immunostaining) and deposition of fat (measured e.g. by oil red/sudan black or adiponectin immunostaining). Advanced age impairs skin physiology and results in reduced elasticity (less elastin staining), lower proliferation and increase rate of differentiation (different distribution of keratins).

Grafted skin after fixation or snap-freezing may be stained using conventional histological dyes or stains, or antibodies or nucleotide probes that directly react with the specific cellular markers or their RNA's or with various types of cells or sub cellular compartments. Not all stains are compatible. Therefore the type of stains employed and their sequence of application should be well considered, but can be readily determined by one of skill in the art. Such histochemicals may be chromophores detectable by bright field microscopy, including phase contrast and differential interference contrast, or fluorophores detectable by fluorescence microscopy or confocal laser microscopy. In general, a cell containing samples may be incubated with a solution comprising at least one reagent, which will directly react with or bind to chemical groups of the target. Some histochemicals must be co-incubated with a mordant, or metal, in order to allow staining. A cell containing sample may be incubated with a mixture of at least one stain that binds a component of interest and another stain that acts as a counterstain and binds cellular constituents other than the component(s) of interest. Alternatively, mixtures of multiple probes may be used in the staining, and provide a way to identify the positions of specific probes.

Conventional methods of biochemistry and molecular biology can also be used for assays in this system. For example, reverse-transcriptase polymerase chain reaction (RT-PCR) or Western blotting can be used to measure changes in human-mRNAs and proteins, respectively in CAM grafted skin response of skin. Other methods, such as flow cytometry and polymerase chain reaction (PCR), are readily available to the skilled artisan, and may be used for determining the presence of such biomarkers.

Other methods of chemical analysis, including, but not limited to HPLC, may be used for determining the presence of a tested chemical in samples taken from the embryo-graft system, as described above.

3.3 Grafting Abnormal or Diseased Skin

In different preferred embodiments, the present invention provides a system comprised of skin explants transplanted onto the CAM, where the explants are taken from skin having a pathological condition.

Possible pathological conditions include but are not limited to psoriasis, cancer, bullous diseases of the skin, xeroderma pigmentosum, seborrheic keratosis, fibrosis, restenosis, wart infection, and acne. Other pathological or abnormal conditions include, but are not limited to, alopecia, chapping, tautness, diabetic ulcers and photoaging. Examples of photoaging include but are not limited to wrinkles, lines, sagging, freckles, discoloration, hyperpigmentation, age spots, thinning of the skin, epidermal hyperplasia, skin elastosis, degradation of the extracellular matrix, precancerous keratoses growths. Examples of bullous diseases of the skin include but are not limited to epidermolysis bullosa and bullous pemphigoid.

The term "alopecia" refers generally to baldness, e.g., the absence of hair from skin areas where it is normally present. Various forms of alopecia are noted in the art. For instance, alopecia greata refers to hair loss, usually reversible, in sharply defined areas, usually involving the beard or scalp; alopecia mediacamentosa refers to hair loss due to ingestion of a drug; and male pattern alopecia, or male pattern baldness, refers to loss of scalp hair genetically determined and androgen-dependent, generally beginning with frontal recession and progressing symmetrically to leave ultimately only a sparse peripheral rim of hair.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidernolytic hyperkeratosis and seborrheic dermatitis. For example, epidermodysplasia is a form of faulty development of the epidermis, such as "epidermodysplasia verruciformis", which is a condition due to a virus identical with or closely related to the virus of common warts. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cells infiltrates into the dermal layer and polymorphonuclear leukocyte infiltration into the epidermal layer resulting in an increase in the basal cell cycle. Additionally, hyperkeratotic and parakeratotic cells are present.

In a particular embodiment, and the system provides methods for screening anti-acne agents. Furthermore, the current invention, which provides a method of testing the irritability potential of many chemical agents, provides a method of screening anti-acne agents for their irritability potential as well by examining, for example, sebum production, follicular keratinization, *Propionibacterium acnes* (*P. acnes*) proliferation, or inflammation (Webster, G. F., "Acne Vulgaris: State of the Science", Arch Dermatol, vol. 135, September 1999).

In yet other embodiments, the skin itself does not actually exhibit a pathological condition, but rather the skin is obtained from a diseased individual. For example, skin of a patient with liver cancer undergoing chemotherapy could be grafted to the CAM, in order to determine the effect of other drugs designed to ameliorate side effects of the chemotherapy on the skin. Another example is a skin having a pathological condition which does not exhibit signs of the pathology before being engrafted (e.g. cancer susceptibility).

It is noted that the invention furthermore provides an especially effective system for screening therapeutic agents for bullous maladies, since for these diseases it is especially important to preserve the normal human dermal-epidermal junctions.

3.4 Expression of Exogenous Genes in Mammalian Skin Explants on the CAM of an Avian Egg.

The current invention is also based, in part, on the surprising experimental finding that it is also possible to cultivate mammalian skin explants transformed by an exogenous oligonucleotide on the CAM, and that there is clear evidence of expression that the exogenous oligonucleotide expresses a recombinant gene product.

In one aspect, the invention provides a model system for introducing genes and gene products into mammalian skin. The skin is an especially attractive target for gene therapy. In particular, the ability to target genes to the epidermis of the skin could be used to correct skin-specific disorders as well as for the production of proteins secreted into the dermis to correct certain systemic diseases. For example, genes expressing cytokines, interferons or other biologically active molecules could be used to treat skin tumors or other lesions. In addition, keratinocytes and fibroblasts in the skin can secrete protein factors which circulate to treat systemic conditions such as hemophilia. Furthermore, some genes code for factors, such as growth factors, cytokines, therapeutic proteins, hormones and peptide fragments of hormones, cytokine inhibitors, peptidic growth and differentiation factors, which can exhibit a positive effect on the progression of the regeneration of wounded dermal tissues. As demonstrated herein, other gene products, such as β-catenin (gi:38519), have a positive effect on the progression of hair generation.

Despite the clear potential in using skin as a target for gene therapy, the major technical problem of an in vivo method of gene delivery remains largely unresolved. There is at this time an unmet need for a method of screening putative techniques for infecting, transfecting and transforming skin cells for gene therapy.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the nucleic acid molecule include promoters, enhancers and polyadenylation signals, as well as sequences necessary for transport of an encoded protein or peptide, for example N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for keratinocyte gene expression can be linked to a gene of interest to confer epidermal-specific expression of that gene product such as loracrin, involucrin, keratins etc. Negative response elements in keratin genes mediate transcriptional repression (Jho Sh et al, (2001). J Biol Chem). Alternatively, a regulatory element which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs. Alternatively, a regulatory element which provides inducible expression of a gene linked thereto can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S, and White, J. H. (1993) Proc. Natl. Acad. Sci. USA 90:5603-5607), synthetic ligand-regulated elements (see, e.g., Spencer, D. M. et al 1993) Science 262:1019-1024) and ionizing radiation-regulated elements (e.g., see Manome, Y. Et al. (1993) Biochemistry 32:10607-10613; Datta, R. et al. (1992) Proc. Natl. Acad. Sci. USA89:1014-10153). Additional tissue-specific or inducible regulatory systems which may be developed can also be used in accordance with the invention.

In a specific embodiment, a variety of methods are known in the art for delivering the nucleic acid sequence to the cells of the mammalian skin, where it is expressed to produce the desired gene product. Such methods may include, for example, constructing the nucleic acid sequence as part of an appropriate nucleic acid expression vector and administering it so that it becomes intracellular, e.g., by infection using a defective or attenuated retroviral or other viral vector (see U.S. Pat. No. 4,980,286 and the Examples hereinbelow), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429-4432).

Other methods of introducing naked nucleic acids into cells include, but are not limited to, calcium-phosphate mediated transfection, DEAE-dextran mediated transfection, electroporation, liposome-mediated transfection, direct injection, biolistic gun infection, and receptor-mediated uptake (Current Protocols in Molecular Biology, Ausubel, F. M. et al. (eds.) Greene Publishing Associates, 1989; Molecular Cloning: A Laboratory Manual, 2nd Edition, Sambrook et al. Cold Spring Harbor Laboratory Press, 1989) and may be utilized for transforming various cell types used in the present invention.

One preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid. Additionally, molecules encoded within the viral vector, e.g. a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) Blood 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .psi.Crip, .psi.2 and .psi.Am. Retroviruses have been used to introduce a variety of genes into many different cell types, including epithelial cells endothelial cells, lymphocytes, myoblasts, hepatocytes, bone marrow cells, in vitro and/or in vivo (see for example U.S. Pat. No. 4,868,116; U.S. Pat. No. 4,980,286; PCT application WO 89/07136; PCT application WO 89/02468; PCT application WO 89/05345; and PCT application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including, for example, airway epithelium (Rosenfeld et al. (1992) cited supra), endothelial cells. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol 57:267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics In Micro. And Immunol. (1992) 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

In one preferred embodiment, the transfection regent ExGene™ 500 (Euromedex, Souffleweyersheim, France) a fully linear member of the polyethylenimine (PEI) family, is used to enhance transformation in conjunction with an adenovirus vector containing an exongeous gene. The Exgene 500™ is a lipid mixture normally used for lipofection of mammalian tissue culture cells with naked DNA. As discussed below in the Examples section, this reagent can enhance the rate at which skin cells are transformed by an exogenous oligonucleotide.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product which is easily detectable and, thus, can be used to evaluate efficacy of the system. Standard reporter genes used in the art include, but are not limited to genes encoding β-galactosidase, chloramphenicol acetyl transferase, luciferase, GFP/EGFP and human growth hormone.

The present invention is based, in part, on the surprising experimental finding that skin explants transformed with an exogenous oligonucleotide and transplanted onto the CAM may express gene products five or more days after the explant is placed on the surface of the CAM.

In one embodiment, the gene can be expressed in the transplanted skin for a period of at least five days. One possible application is to screen gene therapy techniques for human skin.

In certain embodiments, the explant is obtained from skin having a pathological condition, as described above.

3.5 Cultivating Mammalian Skin Grafts on the CAM in the Presence of Exogenous Cells.

According to another aspect, the present invention provides a chimeric model system for testing biological processes involving intact mammalian skin in the presence of exogenous cells.

An important aspect of stem cells research in general, and embryonic stem cell research in particular, is the determination of the developmental potency of the stem cells. The most important example, is the establishment of pluripotency of embryonic stem cells. Since these cells are often passaged many times, and undergo genetic manipulations, the possibility arises that mutations arise that prevent subsequent differentiation into the full spectrum of their normal progeny. Two main techniques used today for determination of pluripotency are 1) in-vitro formation of embryoid bodies and 2) in-vivo production of teratomas. Although the in-vitro technique can produce cells from all three embryonic germ layers and germ cells, the differentiation is not as robust as in teratomas. Teratomas are currently made by injecting stem cells into muscles or the kidney capsule of immune-compromised mice.

The invention provides chimeric systems and methods useful for determining stem cell potency by measuring teratoma formation in the skin explant grafted on the CAM. The presence of different differentiated cell types can be tested for using immunocytochemistry for cell/tissue specific antigens. In order to distinguish the host skin cells from those derived from the transplanted stem cells, genetic markers such as GFP can be used, or by performing in-situ hybridization for sex-chromosomes (e.g. using Y-chromosome probe for XY-derived embryonic stem cells transplanted to female breast skin on the CAM). If the stem cells are from a non-human source, analysis can be performed with molecular techniques such as gene arrays, RT-PCR etc.

Other uses for this system include, but are not limited to, examining pathogen infection in mammalian skin, determining the metastatic ability of cancer cells, and determining the roles of different cells in wound healing.

In various embodiments, the exogenous cells may be mammalian cells or non-mammalian cells. In the event that non-mammalian cells are introduced to the system, possible cell types include infectious microbes, such as fungi or bacteria or eukaryotic parasites.

In various embodiments, the exogenous cells may be introduced into the explant by topically applying them to the skin explant or by injecting them either skin vasculature or into egg vasculature.

In one particular embodiment, the exogenous cells are stem cells. Possible types of stem cells include, but are not limited to, cord blood cells, peripheral blood cells, bone marrow cells, dermal cells, epidermal cells, neural cells, embryonic stem cells, and fat stem cells.

In yet another embodiment, the exogenous cells are cancer cells. Growth of cancer cells in the grafted skin could be used for study of subsequently applied anti-cancer agents, metastases of the tumor cells to the chick embryo, the growth of human cancer cells in a human environment, and the effects of cancer cells on neighboring cells of the explant.

In certain embodiments, for example where the skin and exogenous cells are derived from the same organism precluding the use of species specific markers for distinction of the skin cells and exogenous cells, the explant is obtained from a female and the exogenous cell is obtained from a male. In alternate embodiments, the explant is obtained from a male and said exogenous cell is obtained from a female.

4. CHIMERIC SYSTEMS AND METHODS FOR LARGE-SCALE SCREENING OF ANTI-CANCER DRUGS FOR HEMATOPOIETIC NEOPLASTIC DISORDERS

Human blood malignancies, particularly leukemias and lymphomas, are currently treated with standard regimens of chemotherapy. For many patients this therapy is sufficient to induce remission. However, there are situations in which the standard protocols are not sufficiently effective in reducing the number of malignant cells, and for those a solution is being searched for. More specifically, certain patients respond poorly, or do not respond to the conventional drugs currently used in chemotherapy. Moreover, many patients relapse after successful remissions, and often relapsed patients need a different protocol for effective second stage chemotherapy.

In order to overcome this problem, the current inventors have developed a chimeric animal model system for the effective and rapid screening of chemotherapeutic, or anti-cancer, drugs. The animal model system consists of inoculating mammalian, preferably human, hematopoietic malignant cells in avian embryos, and testing anti-cancer or chemotherapeutic drugs for its capacity to kill the engrafted cells. The drug showing the most effective killing of the cancer cells shall then be used for the treatment of the patient from whom the cells were obtained or in other patients with similar disease.

In one embodiment, the animal model described in the invention is for testing chemotherapeutic or other anti-cancer drugs aimed at drug-resistant or -relapse treatment of blood and lymphoid malignancies. In a second embodiment, the present invention relates to an animal model for testing the presence of residual cancer cells in patients post-chemotherapy and/or radiotherapy and/or antibody and/or any other anti-cancer treatment.

A third embodiment involves prescreening of new or combinations of anti cancer agents on malignant blood and lymphoid cells derived from diseases known to be unresponsive to conventional or particular treatments.

Preferably said avian embryo is a chick, turkey or duck embryo, but other avian species like the Japanese quail or birds with a longer incubation period, like the ostrich, may also be used.

4.1 Grafting Malignant Hematopoietic Mammalian Cells to Avian Embryos.

Delivery of the mammalian cells to the avian embryo may be effected through a variety of methods, as described below in the Example 11. Specifically, the cells to be engrafted may be delivered by the following ways:
 (a) intravenous injection into the chorioallantoic blood vessels;
 (b) intracardial injection;
 (c) intraperitoneal injection;
 (d) layering the cells on the chorioallantoic membrane;
 (e) injecting into a blastocyst/early organogenesis stage embryo, from 1 to 3 days of development;
 (f) injecting into the yolk sac;
 (g) injection into the amniotic sac; and
 (h) subcutaneous injection.

In one embodiment, layering the mammalian malignant hematopoietic cells directly on the chorioallantoic membrane is performed in the presence of one or more clotting agents, including, but not limited to fibrin and thrombin.

It is possible that fresh patient malignant hematopoietic cells of certain patients could be less aggressive than others or than common laboratory lines, and therefore may not engraft at detectable levels. In these cases, murine stromal cell lines such as MS-5 or others that are known to support human hematopoiesis, can be used to enhance engraftment of malignant hematopoietic cells using several techniques. In various embodiments, unmodified stromal lines, or cells engineered to secrete human cytokines/homing factors such as IL-3 or SDF-1 may be used.

Conditioning of hematopoietic stem cells and ALL cells with SDF-1 and stromal cells has been shown to improve their engraftment to the bone marrow of NOD-SCID mice. Thus, in certain embodiments, malignant hematopoietic mammalian cells (e.g. human leukemia cell lines or patient hematopoietic malignant cells) are cultured with murine or other mammalian stromal cell lines that support human hematopoiesis, and then grafted to avian embryos intravenously.

Co-grafting several types of cells, including cord blood mononuclear cells and stromal cells, has been shown to improve human hematopoetic/leukemic engraftment in NOD-SCID mice. In other embodiments, malignant hematopoietic mammalian cells are co-injected with murine or other mammalian stromal cell lines that support human hematopoiesis, and then grafted to chick embryos intravenously.

Addition of cytokines and homing factors to the bloodstream of NOD-SCID mice has been shown to enhance human hematopoietic/leukemia cell engraftment. The chick chorioallantoic membrane (CAM) has been utilized to grow tumors of adherent cells for many years. In yet other embodiments, malignant hematopoietic mammalian cells are injected into the amnion of early embryos, and upon the maturation of the CAM a few days later, mammalian stromal cells that support human hematopoiesis are grafted to the CAM for constitutive secretion of leukemia supporting factors to the embryos' blood.

The grafted embryos may be pretreated with irradiation, changes in oxygen or temperature, chemokines, cytokines, DNA altering drugs or antibodies prior to the grafting of malignant cells.

4.2 Drugs and Treatments

Following the validation of engraftment of the hematopoietic cells (see 4.3 below), a drug or treatment of interest is administered to the avian embryo.

Several routes of administration may be examined, including, but not limited to, injection into the albumin sac, injection into the air sac, dripping on the CAM (Mortell et al., 2003. Pediatr. Surg. Int. 19: 359-364), as well as injection into the yolk sac and intravenously.

In various embodiments, the drug can be administered to the malignant cells before or after transplantation at one or various time points. The drug can be administered alone, after or in combination with other anti neoplastic agents or pro engraftment agents, or agents which cause changes in chromatin structure, methyltaion or acetylation of DNA.

The drug can be administered to animals before or after grafting of the malignant at one or various time points.

In certain embodiments, an array of test drugs is first applied to hematopoietic malignant cells for a determined period in vitro, and the drugs which were able to effectively reduce the number of cells by at least 20% preferably at least 50% and more preferably at least 70% are pursued onto the next step, in vivo.

4.3 Detecting Mammalian Hematopoietic Malignant Cells in the Embryo.

In certain embodiments, the malignant hematopoietic mammalian cells are transformed to express an easily-detectable gene marker, in order to easily follow engraftment visually and by FACS and PCR. For example and without limitation, a lentiviral GFP-expression vector (Invitrogen or a similar supplier) may be used to infect patient cells or other malignant hematopoietic mammalian cells before transplanting them to chick embryos. For other hematopoietic cells, such as hematopoietic malignant cell lines, other transformation methods may be used, including, but not limited to those mentioned in section 1.4 above. Several non-limitative examples for detecting the grafted cells in the embryo are described in the Examples below.

Immunohistochemistry may be used for the detection of mammalian proteins within cells verifying (and confirming) their mammalian origin. Exemplary human marker proteins to be detected may be CD45, CD71 (RBC), CD42 0r CD41 (Platelet-megakaryocyte) CD33, CD13, CD14, CD11b, CD15 (Myeloid) CD5, CD3, TdT, CD19, CD20, or CD56 (lymphocytes), CD34, CD133 (early progenitor and stem cell), depending on the type of cells transplanted.

In other embodiments, the tumors are harvested and assayed for increased differentiation and/or apoptosis of the cancer cells. This will be performed, without limitation, by methods such as Wright staining (evaluation of differentiation of cancer cells) or Hoechst nuclear staining/TUNEL staining for apoptotic cells in the tumors (Gavrieli, Y., 1992, J. Cell Biol. 119(3): 493-501).

In parallel, the bone marrow and spleen are harvested, and DNA/RNA extracted and quantitative PCR performed, to see if there are lower levels of human cells in these chick hematopoetic organs (a non limitative example is presented below).

The following examples are presented in order to more fully illustrate some embodiments of the invention. They should, in no way be construed, however, as limiting the broad scope of the invention.

EXAMPLES

Example 1

Culturing of Human Skin Explants on the Chorioallantoic Membrane (CAM) of a Fertilized Avian Egg Materials and Methods:

Eggs:

Freshly-laid fertile chicken eggs were obtained from a local farm. Eggs were stored at 15° C. until required, warmed for one hour to room temperature, and then incubated vertically with the point down in a humid atmosphere at 37° C. for 5-10 days before use. On the third day of incubation, the eggs were turned upside down, and a small hole was made in the sharp side of the egg after cleaning with a tissue impregnated with 70% ethanol. This created an artificial air sac so that the CAM can be accessed later on without causing bleeding.

Human Skin:

Human skin that is normally discarded from mastectomies and abdominal surgery was obtained from the Shaarei Zedek hospital in Jerusalem and Tel Aviv Mediccal Center in Tel Aviv. Permission was obtained from the hospitals' Medial ethic committee according to the Helsinki accords. The skin was pinned out in a petri dish with a rubber bottom, and cut into rectangular/square pieces approximately 5-10 mm on each side using scissors, scalpels or dermatological punches. The skin was stored at 15 degrees centigrade in $PBS^{++}$ until grafting.

Basic Skin-CAM Graft Procedure:

Eggs with an artificial air sac were opened with iris scissors in a sterile hood. The ectodermal surface of the CAM was abraded by touching it briefly with a sterile piece of lens tissue to improve the adherence of the graft. Each piece of skin was then gently placed on the CAM and stretched out. The eggs were then sealed with adhesive tape, and returned to the incubator.

Approximately 80% of eggs containing skin grafts survive until the experiment. Of these, human skin grafts "take" in about 80% of cases, and mouse in about 50-60% of cases.

Organ Culture:

3-6 mm diameter punch biopsies of full thickness human skin were cultured at an air-liquid interface on a plastic mesh insert in 12-well culture plates in MEM medium (high $Ca^{++}$), 10% fetal calf serum and antibiotics.

Analysis:

Skin was fixed in 4% paraformaldehyde or Bouin's fluid, paraffin embedded, cut into 6 μm sections and stained either with hematoxylin and eosin (H&E) or immunostained with skin specific keratin antibodies (K10, K14), and counterstained with Hoechst nuclear staining.

Results:

Human skin transplanted onto the CAM integrated and survived, as seen by the data presented in FIG. 2. FIG. 2A shows images of intact human skin after being cultivated on the CAM or in organ culture for 3, 6 and 9 days, and demonstrates that human skin grafted to the CAM is maintained better than in organ culture.

Human skin grafted to the CAM 3, 6, 9 days after transplantation is presented in panels A, D, G. Note the increase of CAM blood vessels (arrows) around the graft. Histology of CAM grafted (panels B, E, H) and organ cultured skin (panels C, F, I): 3 days after transplantation no qualitative differences were observed between transplanted skin (panel B) and skin in organ culture (panel C). 6 days after transplantation, the architecture of the epidermal layers of skin grafted to the CAM is maintained (panel E) while the epidermal layers of the skin in organ culture are thinner and contain many apoptotic cells (panel F). 9 days after transplantation, the epidermis of transplanted skin appears vital (panel H) while that of the organ cultured skin appears necrotic (panel I). Size bars represent 0.05 mm.

Figure 2A:
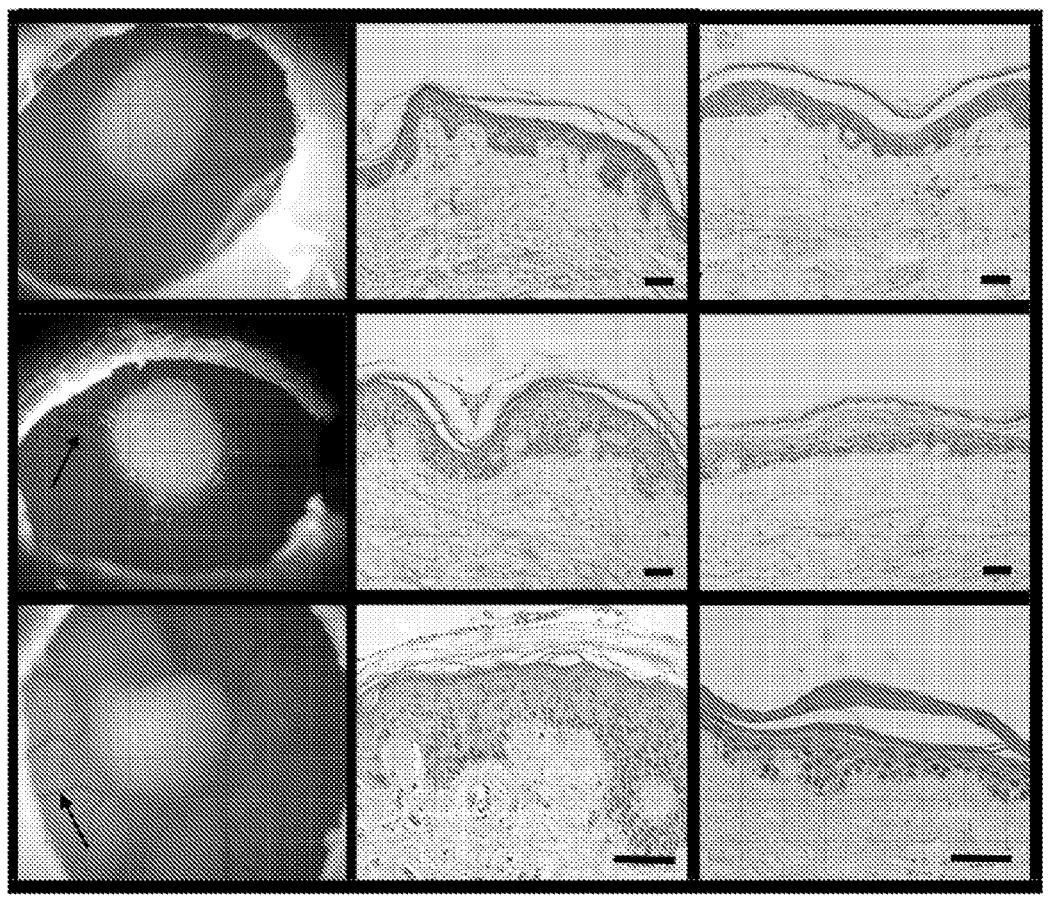
FIG. 2 contains micrographs of intact human skin 3, 6 and 9 days after being transplanted to the chick CAM in comparison to intact human skin organ cultured in vitro for the same period (A), a micrograph demonstrating quantification of epidermal thickness (B), a statistical analysis comparing epidermal thickness in CAM-engrafted and tissue culture-maintained skin (C), and immunohistochemistry staining of the CAM-engrafted skin (D-F).
Figure 2B:
Figure 2C:
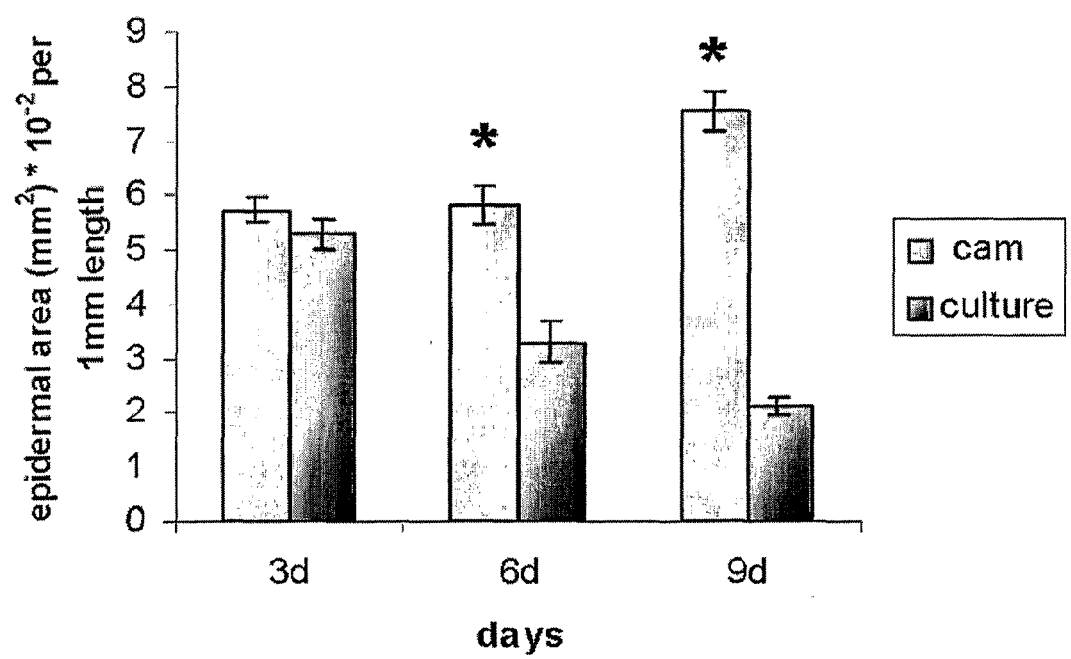
Figure 2D:
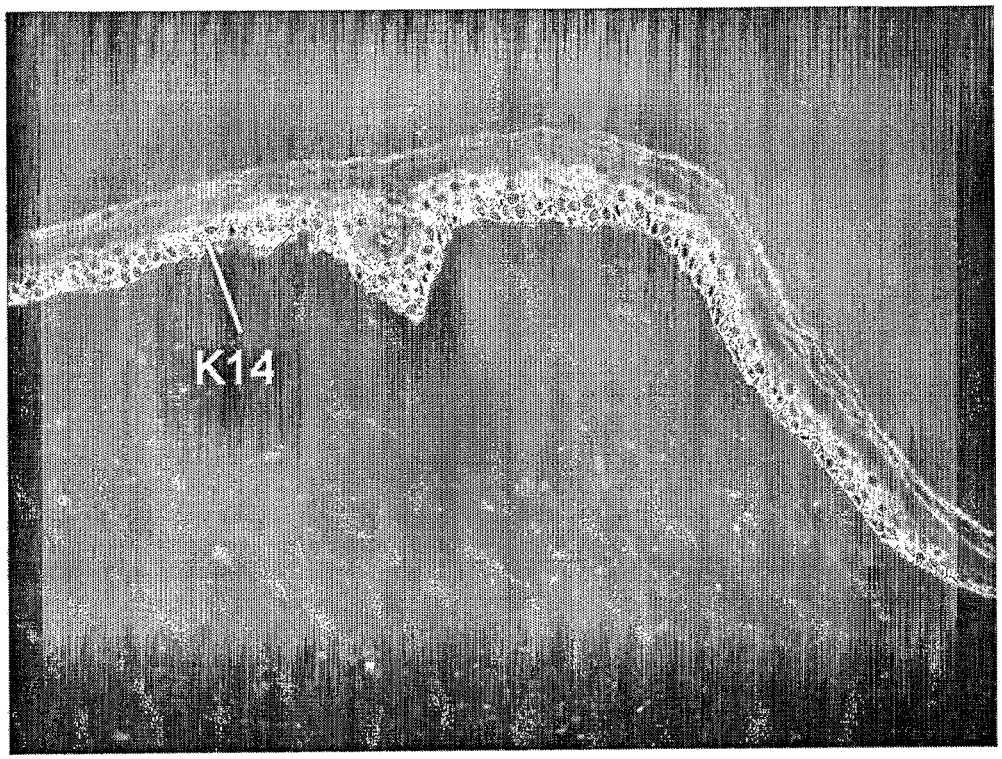
Figure 2E:
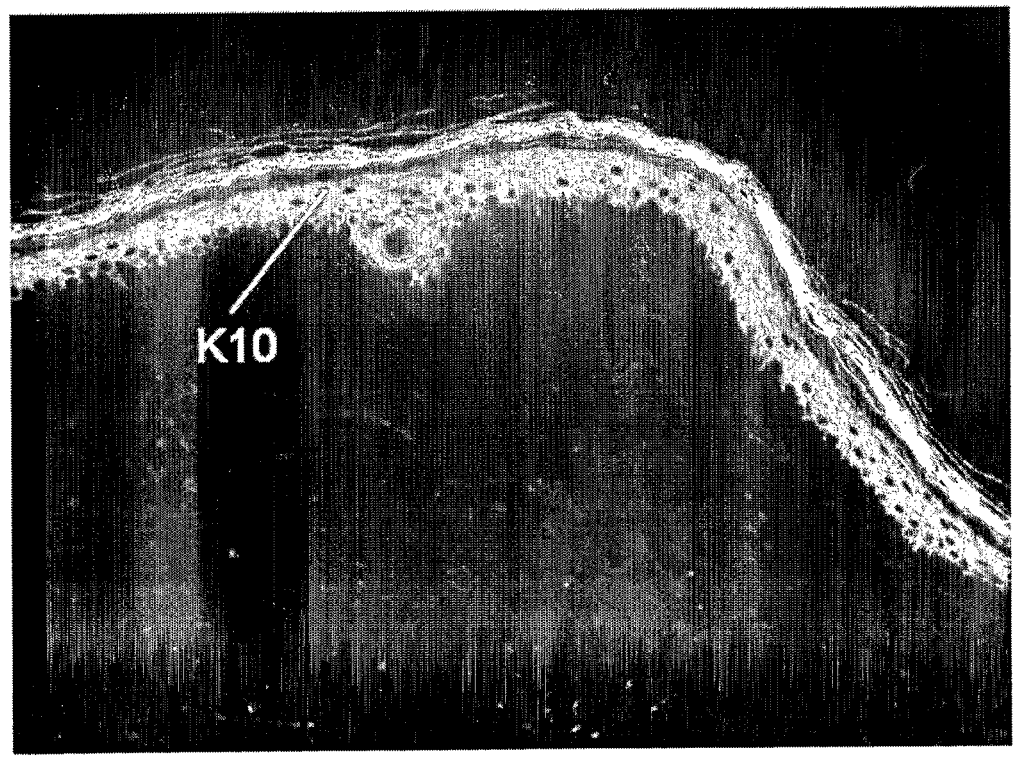
Figure 2F:
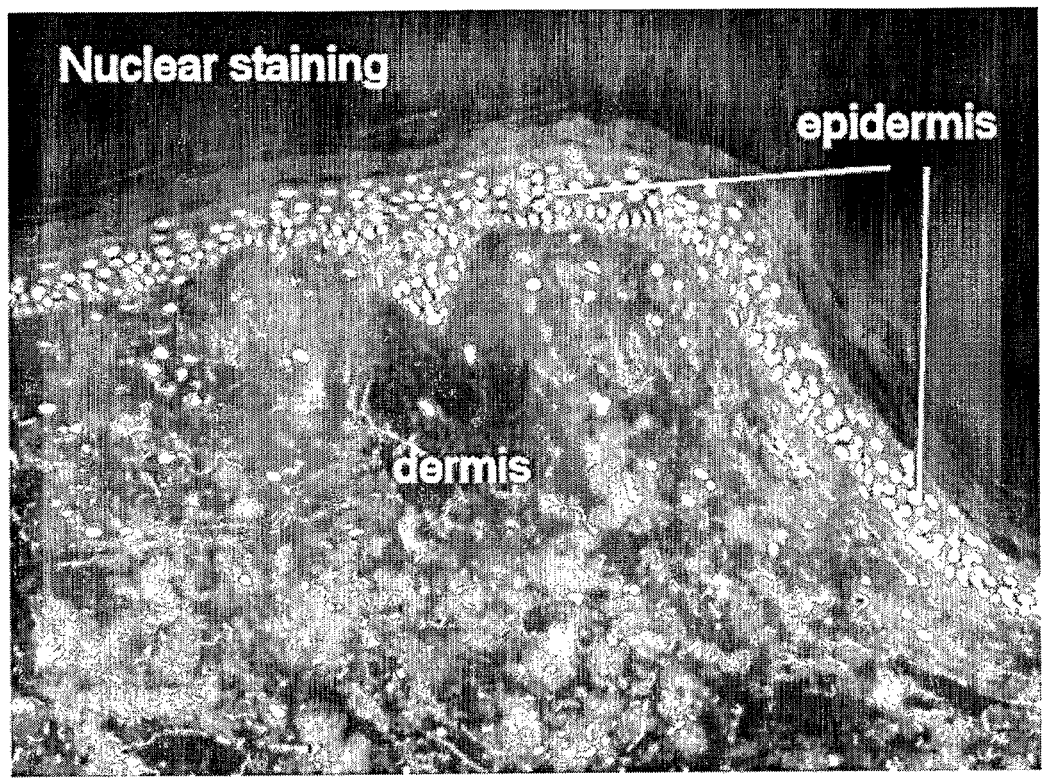

FIGS. 2B and 2C quantitate the change in epidermal thickness of CAM-grafted and organ culture-maintained human skin. Epidermal thickness was measured using digital photos, by tracing the epidermis with a digitizing pad and determining area using the public domain scientific imaging software ImageJ (http://rsb.info.nih.gov/ij/). Size bars represent 0.05 mm FIGS. 2D-2F indicate that skin transplanted onto the CAM for 5 days expressed specific key molecules in the correct layers. It was found that the suprabasal cell layer of the skin transplanted onto the CAM expressed keratin 10 (FIG. 2E), with the expression localized to the suprabasal layers of skin at the end of the grafting period. It was further found that keratin 14 was expressed normally (FIG. 2D), and the nuclear staining (FIG. 2F) also confirmed the normal architecture of the skin graft.

Example 2

Human Skin Irritation can be Quantified Using the Skin-Cam System

Punch biopsies of human skin were grafted onto the CAM of a fertilized egg as described in Example 1. The human skin samples were allowed to incubate for 2 days after grafting in order to allow for the skin to incorporate, and then the adhesive tape sealing of the samples was reopened. The detergent sodium dodecylsulfate (SDS) was applied to different skin samples at different concentrations topically using a small plastic ring cut from a pipette tip keep the irritant in place. The skin samples were then resealed and returned to the incubator for an addition three days, whereupon they underwent routine histological and immunochemical analysis using Abs for the proliferation marker PCNA. PCNA$^+$ cells were counted in several sections, and the length of the epidermis in the section measured. Results are expressed as PCNA$^+$ cells/mm.

Figure 3A:
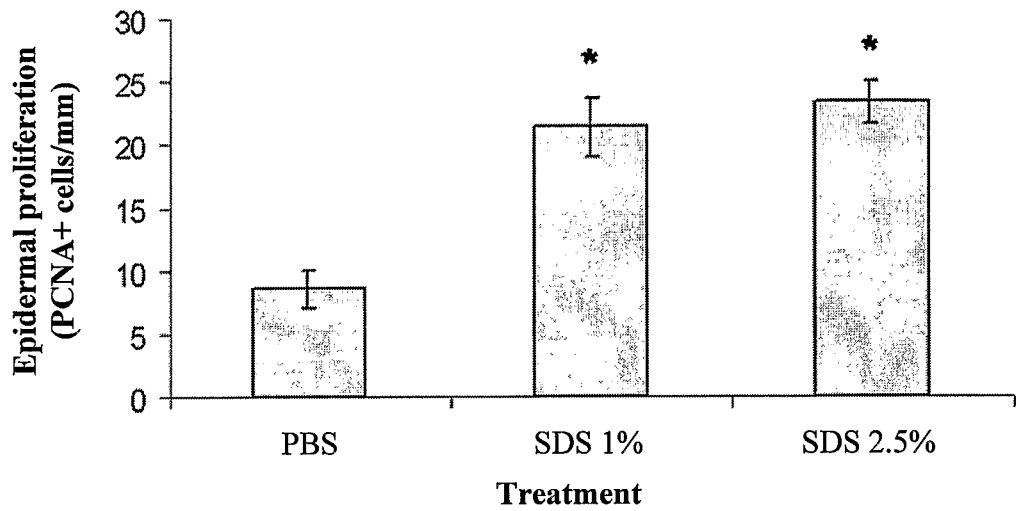
FIG. 3 contains graphs quantifying proliferation (A) and epidermal thickness (B) in SDS treated skin, and micrographs of skin cultivated on the CAM and treated with the irritant SDS (D) or PBS (C).
Figure 3B:
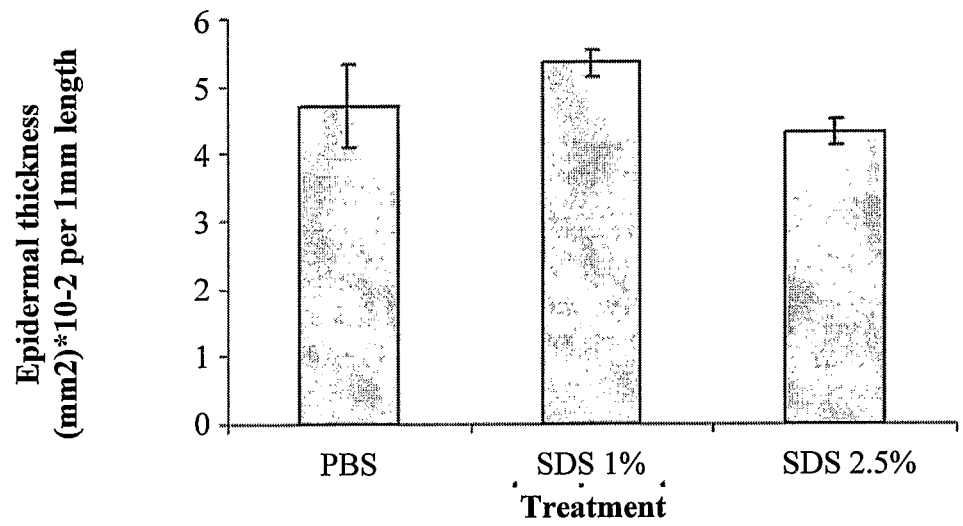

As can be seen in FIG. 3A, SDS, a known irritant, significantly increases epidermal proliferation 3 days after treatment ($p<0.05$). Both 1% and 2.5% concentrations of SDS produce similar results. By contrast, no significant differences in epidermal thickness result from SDS treatment (FIG. 3B), measured as described in Example 2.

Figure 3C:
Figure 3D:
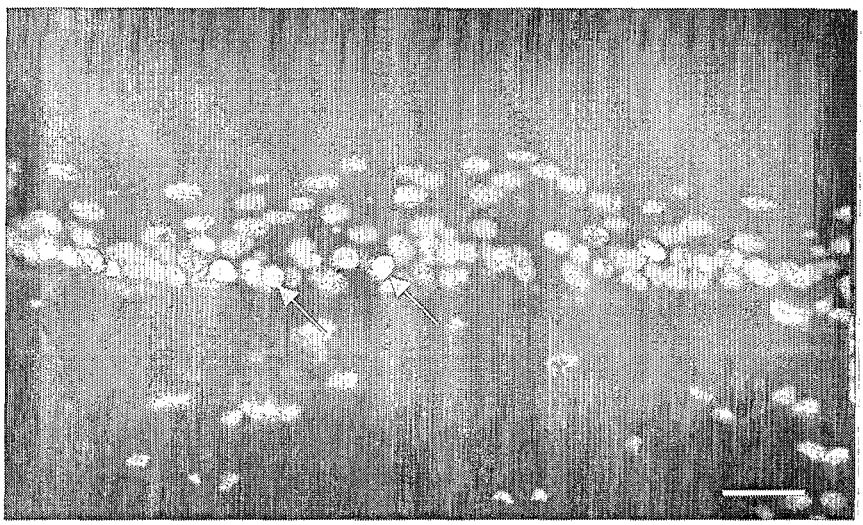

FIGS. 3C and 3D show PCNA staining for dividing cells (arrows, bright cells) in PBS (C) and 1% SDS (D) treated grafts respectively. Nuclei are stained with Hoechst (gray cells). Each size bar represents 0.03 mm.

Example 3

Wound Healing of Both Mouse and Human Skin on the CAM

Wound Healing of Mouse Skin

Mouse skin samples were cut into twenty-five millimeter square pieces, and puncture wounds were produced with a 2.5 mm dermatological biopsy punch. At this point, skin samples were grafted onto the CAM of a fertilized egg as described in Example 1. Up to three samples were grafted into each egg. The skin was then cultivated for an additional 5 days before harvesting for histological and immunocytochemical analysis.

Wound Healing of Human Skin

The above procedure was repeated for human skin.

Results

Figure 4:
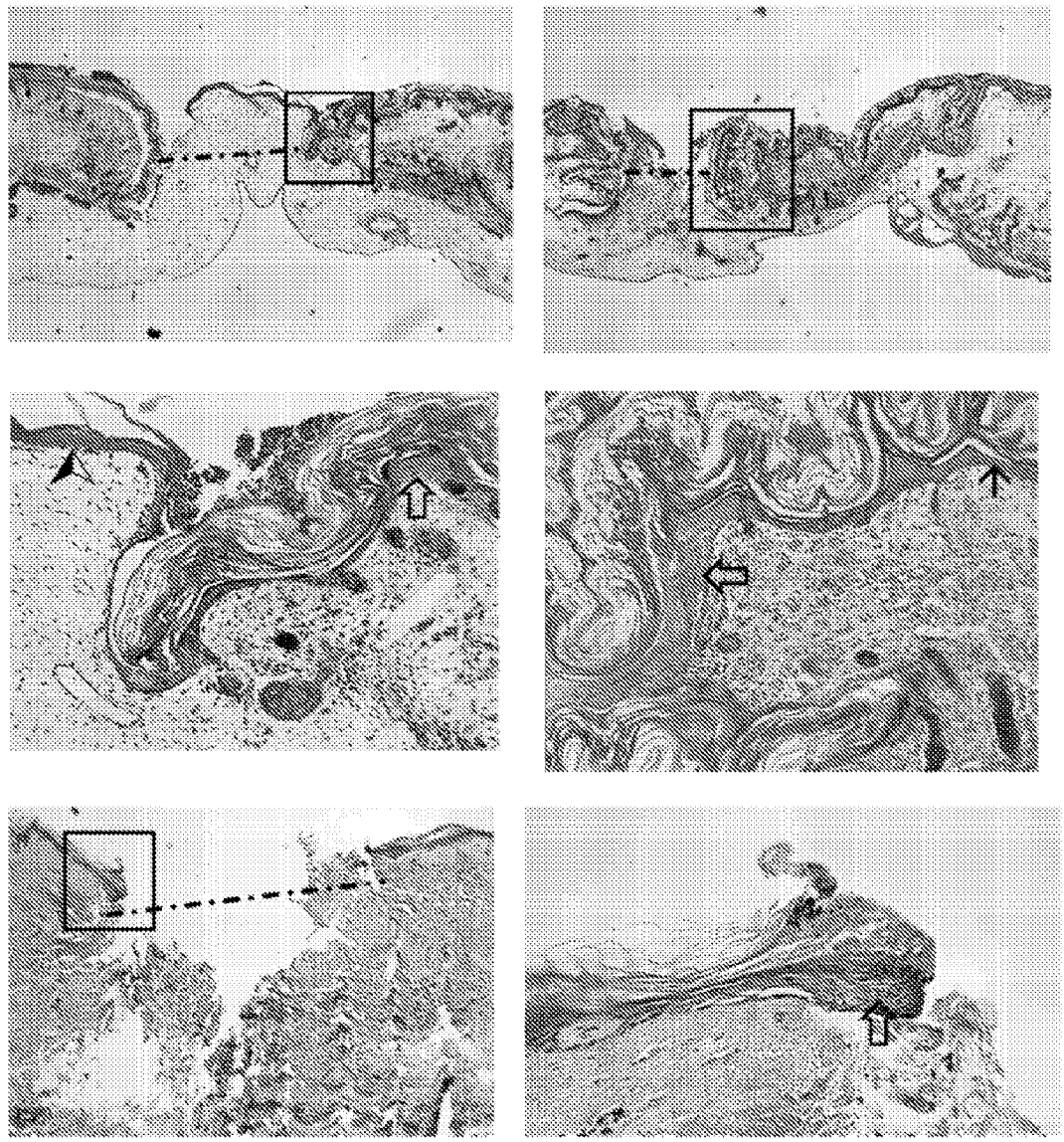
FIG. 4 contains micrographs showing wound healing in mouse and human skin explants transplanted onto the chick CAM.

FIG. 4 illustrates wound healing in mouse and human skin grafted to the chick CAM. Panels A-D show hematoxylin and eosin-stained sections of mouse skin that had been cut with a 0.3 mm punch. In the low magnification images (panels A and B), the opening remaining after healing for 5 days is illustrated by the dashed lines. The boxed areas are enlarged in panels C and D, and the open arrows point to the expanded epidermis that is actively closing the gap in the skin. In C, the arrowhead points to the epithelial layer of the chick CAM. In D, the filled arrow points to the normal thickness of the mouse skin, away from the regenerating zone.

Human skin undergoing wound healing is shown in the micrographs in panels E and F. The much greater thickness of human compared to neonatal mouse skin prevents the chick CAM from filling in the gap (dashed line) left by the hole punch in the human skin (panel E). At high magnification in panel F, the "bulb" of expanded epidermis actively closing the gap is shown by the open arrow.

Example 4

Sunburn Experiments with Human Skin on the CAM

Samples of mammalian skin are cultivated on the CAM as described as in Example 1. Two to three days after grafting, the adhesive tape sealing of the samples are reopened. Some of the skin samples are treated with commercial sunscreens.

Skin samples are irradiated with UV light from a sunlamp or commercial controlled UV source, where the distance between the sunlamp and the skin as well as the exposure time is chosen so as to produce a mild "sunburn" in untreated skin. The CAM and the rest of the egg is shielded with an annulus of opaque material to protect them from heat and UV radiation.

Skin samples are collected 1, 2 and 3 days after irradiation and prepared for paraffin histology. In some experiments, the epidermal surface of the skin is painted with sunscreen solutions before the UV treatments.

In addition, there are two control groups. The first control group consists of skin samples cultivated on the CAM but not irradiated with UV light. The second control group consists of ex vivo skin samples which are not cultivated on the CAM, but are exposed to UV light.

All skin samples including those in both control groups are analyzed using histological and immunochemical techniques. More specifically, UV induced DNA damage, epidermal p53 response and repair kinetics are analyzed as described in Wassberg et al. 2002 (Wassberg, B. et al. 2003, Exp Dermatol 2002:11:349-356). More specially, sections of skin are immunostained for thymidine dimers and p53 (Wassberg et al. 2002).

The above experiment is repeated for Caucasian skin, African skin and Asian skin, sun-exposed (arm) and covered (e.g. breast) skin.

Example 5

Expression of an Exogenous Gene by Mouse and Human Skin Cultivated on the CAM

In this example, it was found that mouse skin infected with an exogenous gene cultivated on the CAM is capable of expressing the exogenous gene for a sustained period of time of at least 3 days.

Materials and Methods

Adenoviruses containing the marker gene coding for green fluorescent protein (GFP; Iyake et al., 1996, Proc. Natl. Acad. Sci. U.S.A. 93, 1320-1324) were grown in 293 cells and concentrated according to standard techniques. Titre of the viruses was determined by infecting keratinocytes in monolayer culture.

Figure 5A:
FIG. 5 contains micrographs showing expression of the green fluorescent protein (GFP) gene in mouse skin explants cultivated on the CAM (A), in a brightfield image (B), a merge of the fluorescence and brightfield image (C), and a histological section through the grafted skin stained with antibodies to GFP (D).
Figure 5B:
Figure 5C:
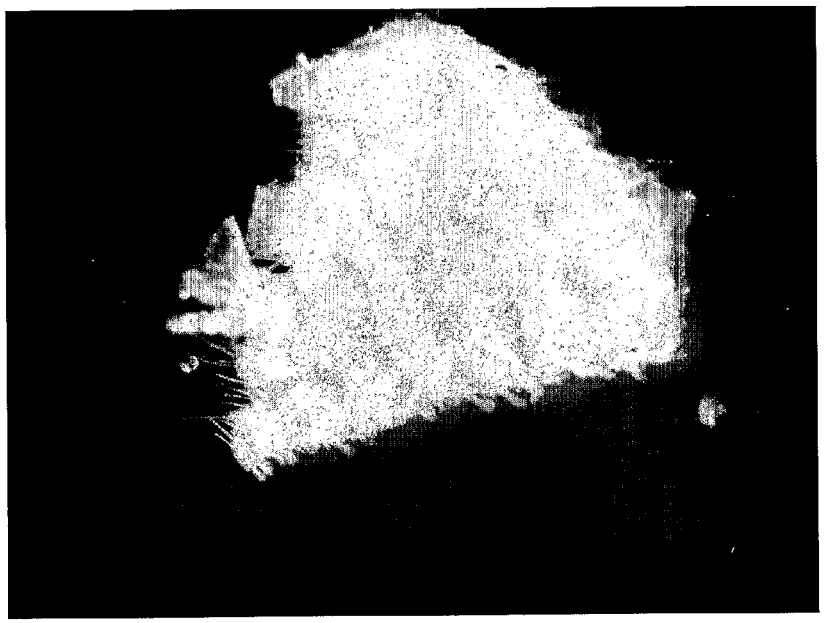
Figure 5D:
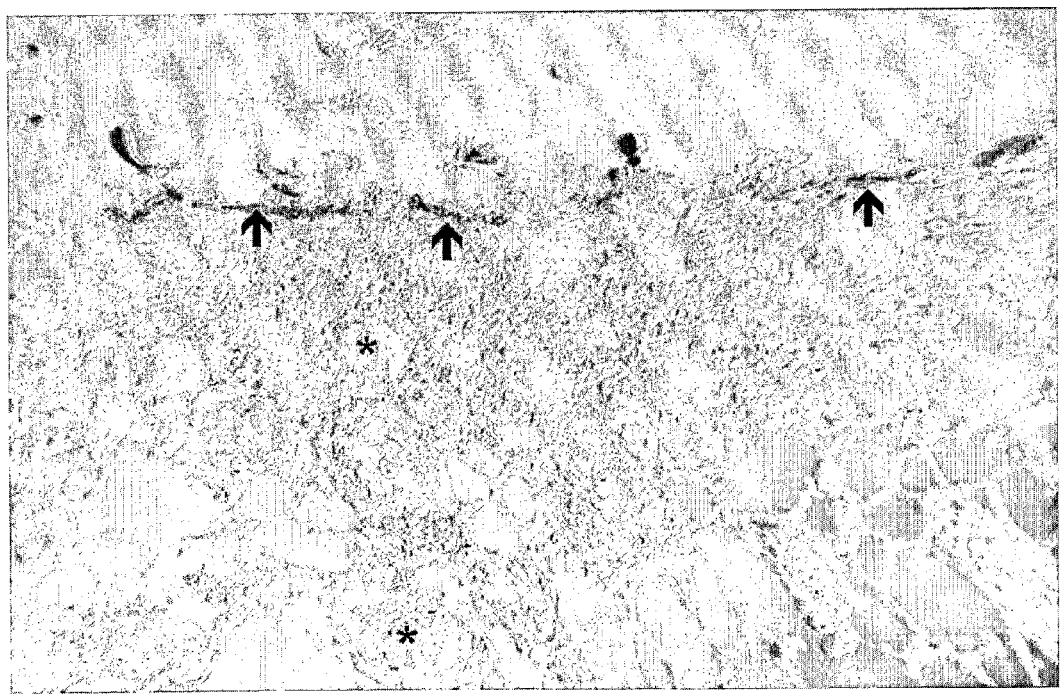

Mouse skin was obtained as described in Example 1, and cut into 25 mm square pieces The pieces of skin were soaked in 2% EDTA at 4° C. overnight. The tissue was then manually teased to partially separate the dermis and epidermis. It was then rinsed, and treated for two hours with adenovirus containing GFP. After 24 hours to allow expression of the viral GFP, the tissue was examined under the fluorescence microscope. FIGS. 5A-5C show an intact piece of skin with large areas of GFP expression. Immunocytochemical detection of the viral GFP shows that it was expressed both in the epidermis and dermis (not shown). When examined histologically, the tissue did not exhibit a healthy morphology. It was hypothesized that the tissue might recover somewhat after grafting and receiving perfusion by the chick's blood. The piece of infected skin was grafted to the CAM for 5 days and examined it histologically and for viral GFP expression. After this period of time, GFP could still be seen in the intact skin after CAM grafting. It appeared weaker than the freshly infected skin, partially because the CAM masked some of the fluorescence, and was therefore difficult to photograph. Nevertheless, immunostaining of sections for GFP showed quite clearly that GFP expression was still present (FIG. 5D).

In FIG. 5A, large areas of infected cells are seen, in dramatic contrast to our initial results where GFP was only expressed at the cut edges of the skin. The skin with its short hairs is seen in a brightfield image in FIG. 5B, and a merge of the fluorescence and brightfield is shown in FIG. 5C.

The piece of mouse skin treated as shown in FIG. 5 A-C was then grafted to the CAM, and incubated for 5 days as described above. The thickness of the skin and the adherent chick membrane precluded photographing the intact skin, but a histological section through the grafted skin stained with antibodies to GFP is shown in FIG. 5D.

The image is presented as a photographic negative, so that the GFP staining is shown in black (arrows). The staining is in the very thin epidermis, beneath which are present many hair follicles cut in cross section, some of which are labeled with asterisks.

Example 6

Increased Hair Growth Caused by Adenoviral Mediated Gene Transfer of β-Catenin to Newborn Mouse Skin Cultivated on the CAM The following example illustrates that hair follicle growth may be enhanced by adenoviral-mediated gene transfer of β-catenin to newborn mouse skin in skin cultivated on the CAM.

Materials and Methods

Balb/C mouse newborn body skin was obtained and cut into 1 cm square explants. To improve penetration of the viruses, the skin was either cut in the center with a circular hole punch, or multiple scratches in the epidermis were made with a scalpel. Both of these procedures increased the number of cut edges and concomitantly the local surface area, enhancing virus penetration.

The samples were incubated overnight with bicistronic adenovirus expression vector (Miyake et al., 1996 Proc. Natl. Acad. Sci. U.S.A. 93, 1320-1324) containing both GFP and β-catenin in a 5% $CO_2$ incubator at 37° C. in Dubecco's minimum essential medium (MEM) with bovine serum albumin (BSA), penicillin, streptomycin and amphotericin, and 1% Exgene 500™ (cationic polymer; MBI Ferment). ExGene™ 500, a fully linear member of the polyethylenimine (PEI) family, is a transfection reagent. The Exgene 500™ is a lipid mixture normally used for lipofection of mammalian tissue culture cells with naked DNA. 200-250 microliters of medium were used in each well of a 24 well tissue culture plate.

In the morning, each explant was rinsed 3 times with phosphate buffered saline (PBS) containing divalent cations ($PBS^{++}$) at room temperature. Each sample was subsequently incubated for 1.5 hours in MEM with high calcium and 10% fetal bovine serum. The explants were then grafted to the CAM of seven day old chick embryos, where each CAM was abraded with a piece of lens paper shortly before each explant was grafted.

One and two days after grafting, the skin was examined in a fluorescence microscope, and the presence or absence of fluorescent cells was noted, in order to get a general impression if the viruses infected. Notwithstanding this examination, the tissue was left for a total of 5 days on the CAM, then fixed and prepared for histology.

Controls: Two control groups were employed in this experiment. For each control group, mouse skin explants were obtained from littermates of the original mouse that contributed the skin. In the first control group, the explants were grafted without being infected with the virus. In the second control group, the explants were infected with the bicistronic adenovirus vector expressing GFP, but were incubated in the absence of Exgene 500™.

Results

1) Viral infection (i.e. gene transfer)—addition of Exgene 500™ significantly increased the number of fluorescent cells observed in whole mounts of skin and in the sections. Immunostaining sections for GFP protein indicated that there was expression both in the epidermal and dermal components of the mouse skin.

2) Effect of β-catenin overexpression on newborn mouse skin.

Skin grafted for five days to the CAM always showed many more hairs and hair follicles than (hairless) newborn mouse skin. This demonstrated that normal maturation transpires in skin explants transplanted onto the CAM, even in samples not infected with the virus.

Furthermore, the overexpression of β-catenin dramatically increased the number of hair follicles in the grafted skin, compared with both the number of hairs observed on explants from both control groups. When sections were immunostained for GFP, many follicles were observed to contain cells that were infected by the virus.

In particular, for the control group whose explants were cultivated in the absence of Exgene 500™, there was both less GFP fluorescence (meaning less viral infection), as well as less enhancement of hair growth than explants incubated in a medium enriched with Exgene 500™.

Figure 6A:
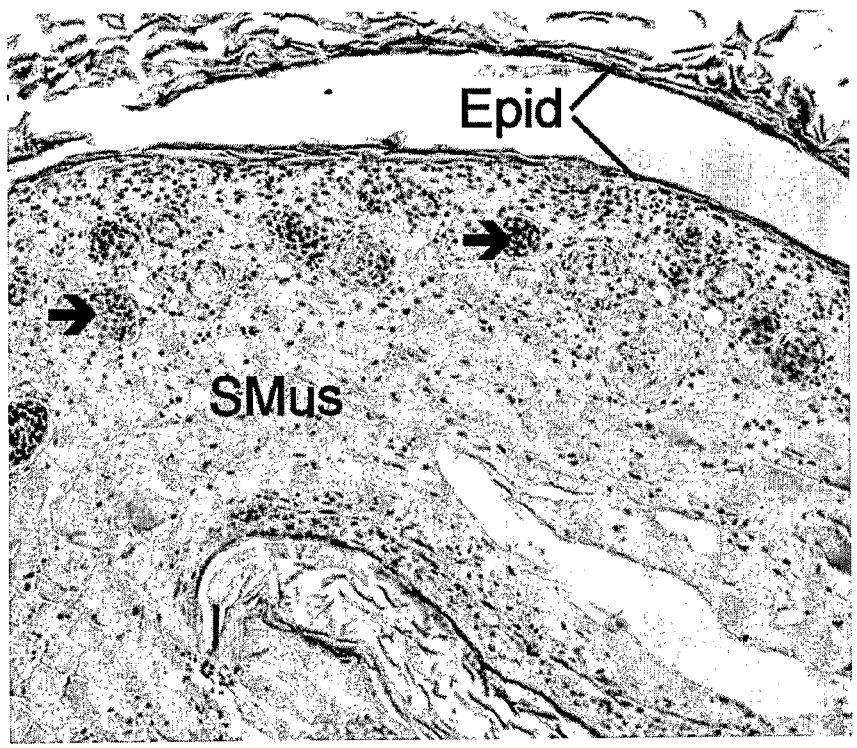
FIG. 6A exhibits a mouse skin explant six days after grafting to the CAM. The epidermis (Epid) and smooth muscle tissue (Smus) are visible.
Figure 6B:
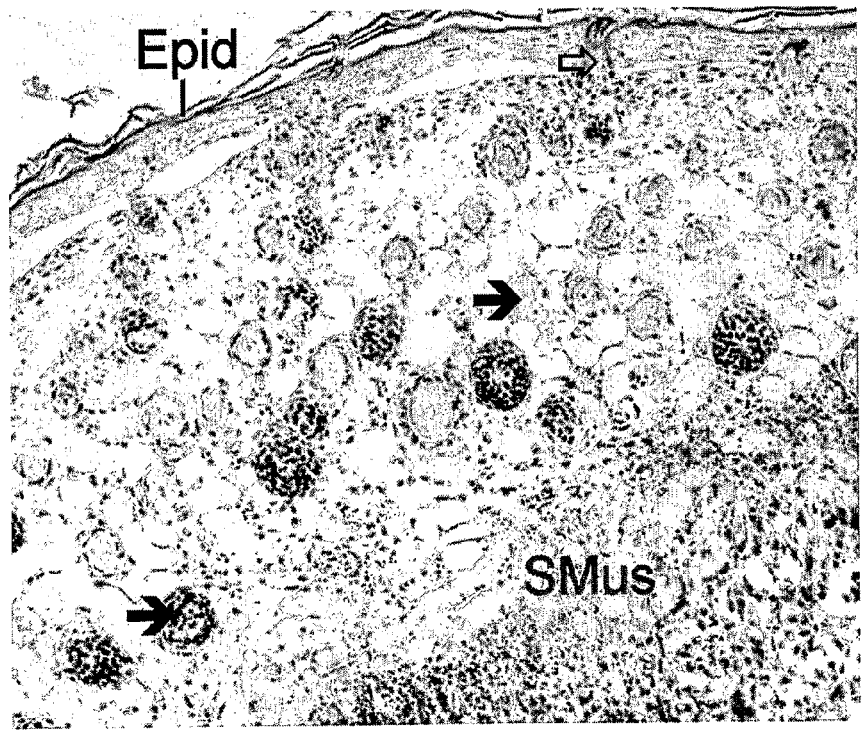
FIG. 6B contains an image of a different skin explant from the same mouse, where the explant of panel B was treated with an adenovirus expression vector containing both GFP and β-catenin in the presence of Exgene 500. The number of hairs (arrows) is higher in the transformed skin (compare FIGS. 6A and 6B).

FIG. 6 illustrates that the overexpression of β-catenin in intact mouse skin results in extensive hair growth. FIG. 6A exhibits a mouse skin explant six days after grafting to the CAM. The epidermis (Epid) and smooth muscle tissue (Smus) are visible. FIG. 6B contains an image of a different skin explant from the same mouse, where the explant of panel B was treated with an adenovirus expression vector containing both GFP and β-catenin in the presence of Exgene 500. The number of hairs (arrows) is higher in the transformed skin (compare FIGS. 6A and 6B). In FIG. 6B, the open arrow indicates growing hair penetrating the surface of the skin. Images in both panels are of paraffin sections routinely stained with hematoxylin and eosin.

Example 7

A CAM Model System for Incorporation of Stem Cells into Mammalian Skin

Human skin explants with a central wound were grafted to the CAM as described in Example 3. After allowing 2-3 days for the blood supply to the skin to become established, a suspension of human embryonic stem cells (line HES-1) constitutively expressing GFP was injected into the dermis of the skin via the opening in the epidermis with a conventional tuberculin syringe. As can be seen in FIG. 11, the GFP-expressing stem cells were incorporated in the skin tissue and could be detected 5 days after their injection into the skin.

Figure 11A:
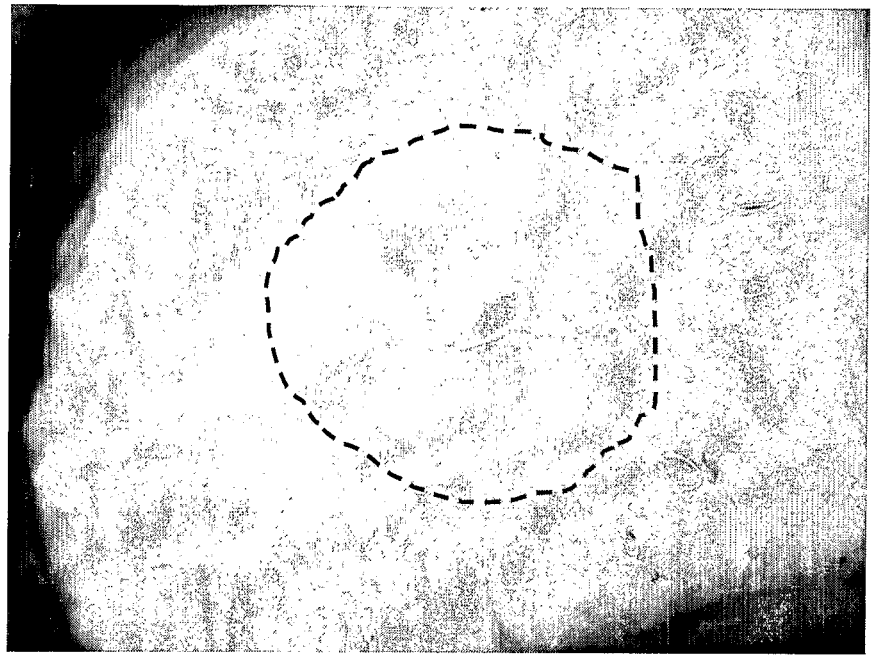
FIG. 11A shows intact skin under conventional illumination. The boundary of the wounded epidermis is marked with a dashed line.

The intact, live skin is seen in FIG. 11A under conventional illumination. The wound in the epidermis has not closed, but the dermis beneath has filled in the wound. The boundary of the wounded epidermis is marked with a dashed line.

Figure 11B:
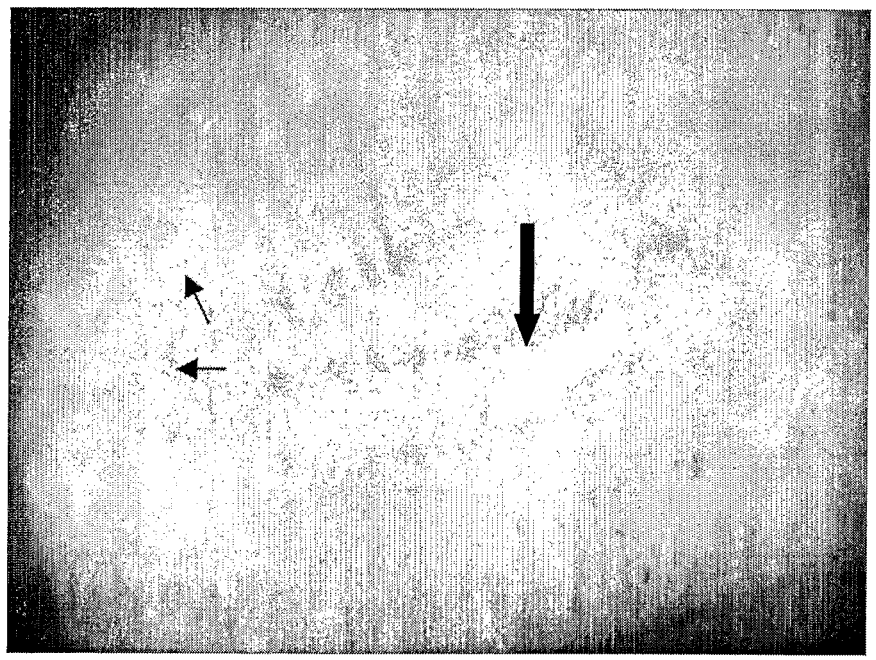
FIG. 11B shows the mass of the stem cells in the graft with strong GFP fluorescence (large arrow) and stem cells that migrated away from the injection site (small arrows).

In FIG. 11B the mass of the stem cells in the graft with strong GFP fluorescence are obvious (large arrow). In addition, some of the stem cells have migrated away from the injection site (i.e. at small arrows in 11B).

For determining the developmental potency of the stem cells, skin, human or murine, is grafted to the CAM as described above, and after allowing 2-3 days for the blood supply to the skin to become established, a suspension of stem cells (e.g. human embryonic stem cells) is injected into the dermis of the skin with a conventional tuberculin syringe. When chicken (*Gallus gallus*) eggs are used, the stem cells are grown in conditions permissive to differentiation (as an adherent culture or as embryoid bodies, both without the mitogen FGF and feeder layers, see, for example Reubinoff et al., Nat. Biotechnol. 2001 December; 19(12):1134-40) for 1-2 weeks before dissociation and injection into the skin. In other experiments, duck eggs with a 6 week incubation period are used, with naïve, undifferentiated stem cells or in other experiments stem cells grown in conditions permissive to differentiation.

The presence of different differentiated cell types is tested using immunocytochemistry for cell/tissue specific antigens, such as albumin for liver cells, insulin for pancreatic beta cells, neurofilament protein for nerve cells, surfactant protein for lung cells, cardiac myosin for heart cells etc. In order to distinguish the host skin cells from those derived from the transplanted stem cells, genetic markers such as GFP are used, or in-situ hybridization for sex chromosomes is performed (e.g. a Y-chromosome probe for XY-derived embryonic stem cells transplanted to female breast skin on the CAM), in combination with the immunostaining or on adjacent sections. In other experiments, mouse stem cells are injected into the human skin explant, and analysis is performed by RT-PCR.

Example 8

The Culturing of Mammalian Skin Explants on the Chorioallantoic Membrane (CAM) of a Shell-Less Fertilized Avian Egg Freshly laid fertile chicken eggs were obtained from a local farm. Eggs are stored at 15° C. until required, warmed for one hour to room temperature, and then incubated vertically with the point down in a humid atmosphere at 37° C. for 48-72 hours before use. The fertilized eggs are subsequently wiped with a tissue soaked in 70% ethanol. The shells of the fertilized eggs are then carefully removed, and the eggs are gently placed into a sterile vessel. Special precautions are taken to ensure that the yolk of the fertilized egg is kept separate from the white.

A first group of the eggs are placed into a standard sterilized Pyrex bowl about 10 cm in diameter. A second group of the eggs are placed into a cling film bag within a Styrofoam cup. The first or the second group of eggs are subsequently covered with an inverted petri dish. The first or the second group are covered with more cling film held with a rubber band. The shell-less embryos are returned to the standard incubator for further growth.

After being further incubated for an additional 2-5 days, the eggs are removed from the incubator, and opened. Mammalian skin explants, prepared as specified in Example 1, are placed onto the surface of the CAM. The eggs are subsequently resealed and returned to the incubator.

Figure 7:
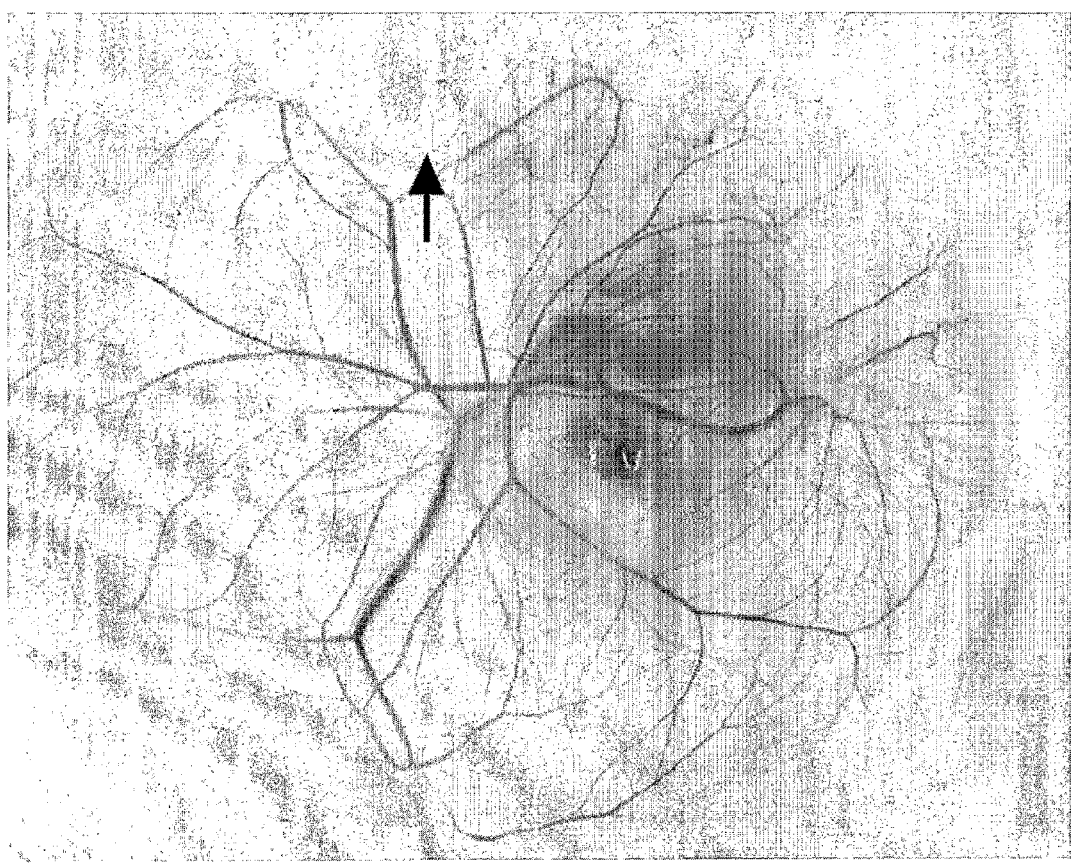
FIG. 7 illustrates the growth of a chick embryo in a shell-less culture.

FIG. 7 demonstrates a shell-less chicken egg culture in a standard sterilized Pyrex bowl about 10 cm in diameter. Note the highly vascularized structure of the CAM. The arrow indicates a small plastic ring cut from a pipette tip, into which the skin graft is inserted and the external modulators applied.

Example 9

Activation and Mobilization of Langerhans Cells (LC) in Human Skin Models Treated with Contact Sensitizers and Antigenic Molecules Excess fat was manually removed from human skin obtained within 2 hours of surgery. The skin was cut into rectangular/square pieces approximately 7-10 mm on each side and stored on a cold plate at 15° C. in saline. Eggs with an artificial air sac were opened with iris scissors in a sterile hood. The ectodermal surface of the CAM was abraded by touching it briefly with a sterile piece of lens tissue to improve the adherence of the graft. The skin was then gently place on the CAM and stretched out. The eggs were then sealed with scotch tape, and returned to the incubator.

Two-three days after grafting the skin, the eggs were re-opened, and the grafts are evaluated visually for viability. Eggs containing skin that has yellowed or that looks obviously infected were discarded. A plastic ring just smaller than the skin was placed on the graft in order to prevent leakage of the test substance away from the skin, using Vaseline to seal it down. Then, a 50 µl drop of the tested substance was placed on the skin, and the egg was re-sealed and incubated for another 6 hours-5 days. At the end of the re-incubation, the skin was removed from the CAM and prepared for paraffin histology.

The skin and a small portion of the (non-innervated) CAM was dissected out into cold saline, and then transferred to fixative. The skin was then dehydrated through a series of alcohols and embedded in paraffin. Sections were then made and mounted on Super-Frost Plus slides and the slides baked at 60° C. for 30'. Some slides were stained with hematoxylin and eosin for rough determination of the quality and survival of the tissue. Other slides were stained immunocytochemically to detect various tissue antigens using microwave antigen retrieval. Stained sections were examined in a fluorescent microscope (or confocal laser scanning microscope) and photographed digitally All the microscopic 400 µm-fields in triplicate sections from each skin sample were counted with a 40× objective. The average number of cells per field was then determined and averaged for that skin sample. At least 4 skin samples were used per treatment and each experiment was performed at least twice.

In the experiments presented in FIGS. 8, 9 and 10, skin grafts were treated with the contact sensitizer dinitrofluorobenzene (DNFB) or with lymphotoxin (LT), respectively, and subsequently stained with an Ab recognizing the LC marker CD1a.

Figure 8:
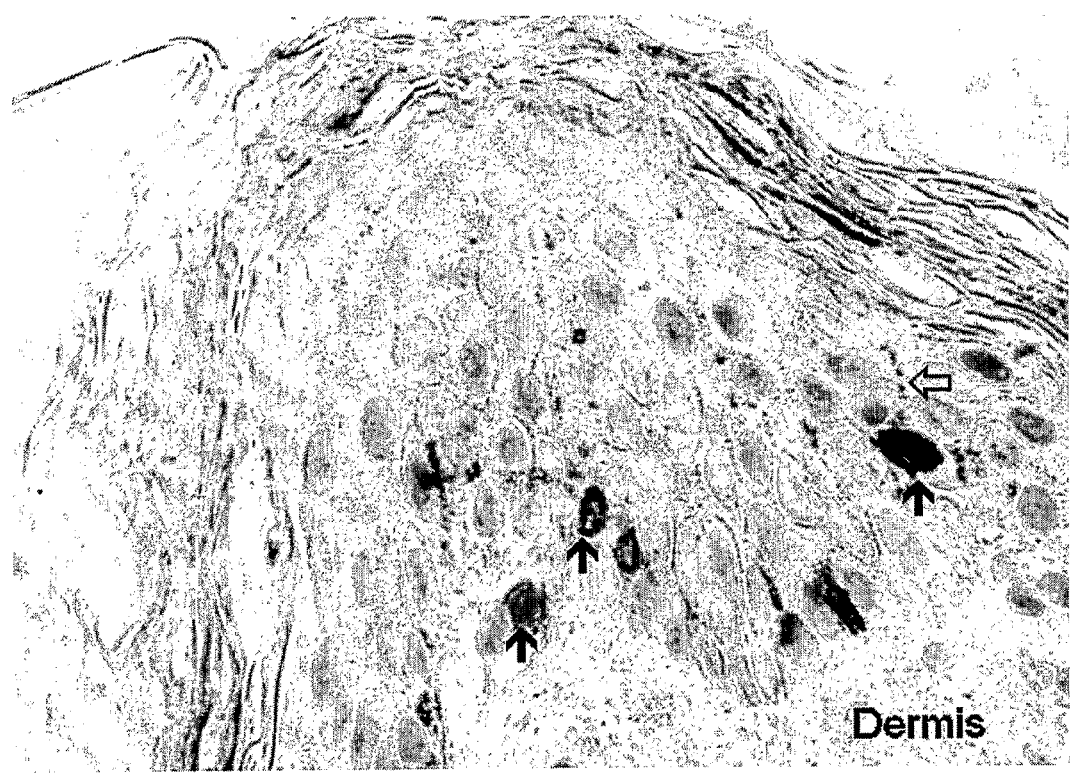

FIG. 8 is a photomicrograph of a section stained immunocytochemicallly for CD1a, a marker for dendritic immune cells in human skin grown on the CAM for 5 days. Several of the stained epidermal dendritic cells, or Langerhans cells (LC), are indicated by solid arrows. The open arrow at the right of the picture indicates a stained process of one of the LC. The dermis (Dermis) is at the bottom of the picture.

Figure 9:
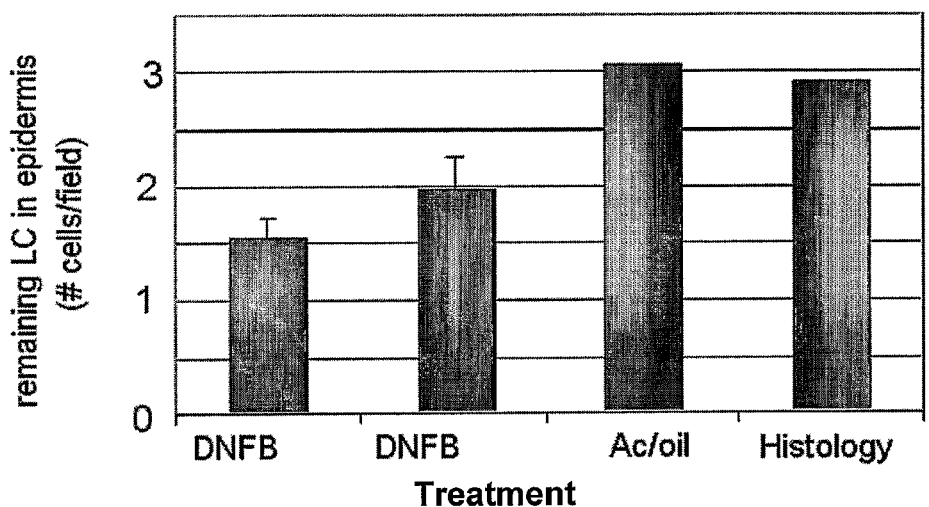
FIG. 9 demonstrates that LC in human skin explants cultivated on the CAM respond to the contact sensitizer dinitrofluorobenzene (DNFB).
Figure 10:
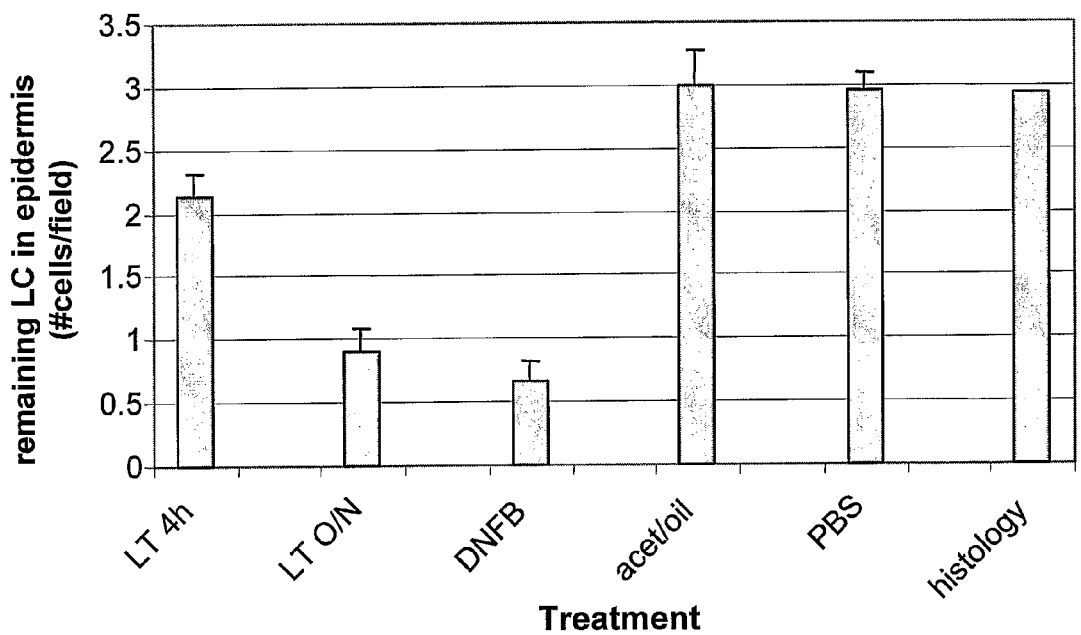
FIG. 10 demonstrates that LC in human skin explants cultivated on the CAM respond to lymphtoxin (LT).

As can be seen in FIG. 9, upon the treatment of skin grafts with DNFB, a significant decrease of CD1a$^+$ LC in the epidermis was observed after overnight (O/N) incubation, when compared to untreated skin fixed immediately (histology) or O/N acetone/olive oil (solvent) treated skin. Treatment of skin grafts with LT also resulted in a clear decrease in the number of CD1a$^+$ LC in LT-treated epidermis (FIG. 10). This reduction in CD1a$^+$ cells in the epidermis indicates migration of CD1a$^+$ LC to the dermis or bloodstream.

The presence of epidermal LC in the dermis is determined by staining sections of dissected treated skin with anti-Langerin/CD207 antibodies (Abs). Initiation of the homing process to the spleen is examined by staining the sections with anti-CCR7 Abs and counting CCR7$^+$ cells in the skin. DC maturation is examined by staining the skin sections with Abs to CD83, which is a maturation marker for DC.

For examining LC homing to the spleen, PCR detection of migrated human cells is performed as follows: A few days after grafting skin and treatment with sensitizers such as DNFB, the spleens from the chick embryos are dissected, and genomic DNA is extracted using puregene (Gentra). The presence of human-specific DNA within spleens (chick embryos do not have lymph nodes) of transplanted chicks is confirmed by polymerase chain reaction (PCR) amplifying an 850-bp fragment of the a-satellite region of the human chromosome 17.

In other experiments, the effects of the tumor-associated antigen HR-gp100 on LC activation and mobilization are determined and analyzed as described above.

Example 10

Engraftment of the Leukemic K562 Cell Line in Chicken Embryos

Methods:
Cell Line:
The K562 CML line was maintained in Iscove's medium containing 10% heated-inactivated fetal calf serum, 1 mM L-glutamine, and antibiotics. A line of K562 constitutively expressing GFP was made by electroporation of a commercial plasmid (eGFP, Clonetech) and antibiotic selection.

Transplantation of K562 Cells to Chick Embryos:
Four different methods of transplantation of leukemia cells were attempted:
1) The amniotic sac of three-day chick embryos was injected with $0.5 \times 10^6$-$2 \times 10^6$ K562 cells.
2) The yolk sac of three-day chick embryos was injected with $3 \times 10^6$-$6 \times 10^6$ K562 cells.
3) Intravascular injections of K562 cells were made into chorioallantoic vessels of eleven-day chick embryos.
4) $0.25 \times 10^6$-$1 \times 10^6$ K562 cells were inoculated on the CAM of the 9-10 day chick embryos.

FIG. 1 is a schematic representation of a cross-section through a chick egg of about 9 days incubation. The chorioallantoic membrane (CAM) with its large blood vessels, amnion and yolk sac are labeled.

PCR Detection of Human Cells:
Samples of spleen, liver and bone marrow were dissected from 18-day-old chick embryo and genomic DNA was extracted using Puregene (Gentra). The presence of human DNA within organs of transplanted chicks was confirmed by polymerase chain reaction (PCR) amplifying an 850-bp fragment of the a-satellite region of the human chromosome 17.

Immunocytochemistry of Human Cells:
CAMs containing tumors were fixed and stained with mouse anti-human mitochondria antibody (Chemicon) and detected using fluorescent secondary antibodies.

Flow Cytometry Analysis:
Antibodies to human CD markers are used to label a population of cells, such as the pan-leukocyte marker CD45 (for leukemia cells), CD71 (for the K562 line), CD41 (for the megakaryoblastic cell lines). At least 50,000 events per sample are acquired to detect the presence of human leukemia cells with a BD FACS Calibur (BD Bioscience) and data analyzed with Cell Quest and Cell Quest Pro software (BD Bioscience). In some experiments, positive selection for the grafted cells is performed by using GFP-labeled cells.

Figure 12A:
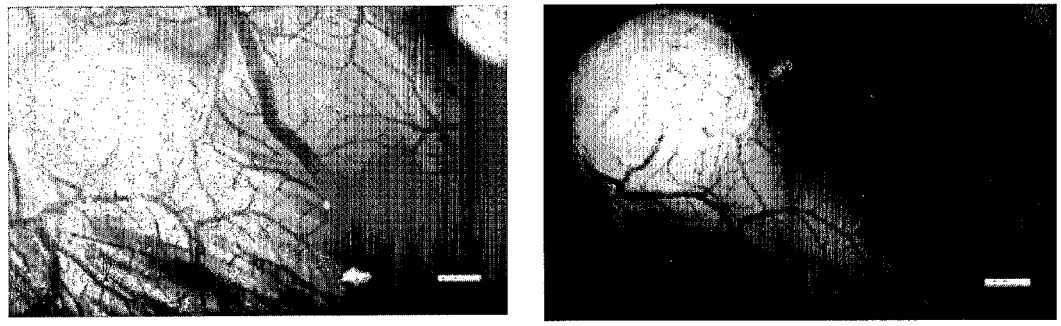
FIG. 12 demonstrates that human leukemia K562 cells produce solid tumors on the CAM of the chick embryo when administered topically (A) or intravenously (B), using bright field (left panel) and fluorescence illumination (right panel).
FIG. 12C depicts the boxed area of FIG. 12B at higher magnification.

As can be seen in FIG. 12A, K562 cells produce solid tumors on the CAM of the chick embryo when administered into the amniotic sac. GFP-expressing K562 cells were injected into the amniotic sac of the embryo and 14 days later, a large tumor that is visible in both bright field (left panel) and in fluorescence illumination (right panel) has formed. Scale bars represent 1 mm.

Figure 12B:
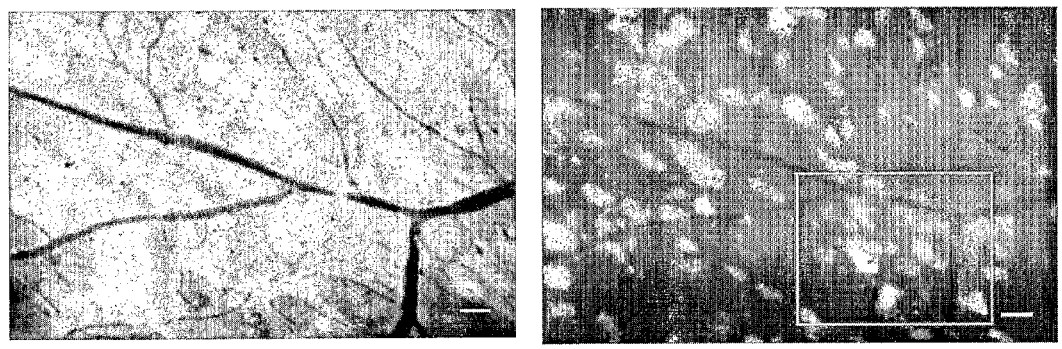
Figure 12C:
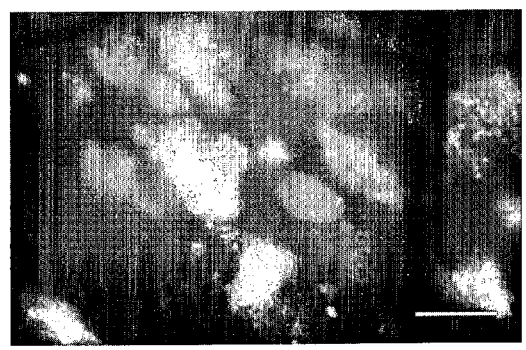

FIGS. 12B and 12C demonstrates tumor formation following intravenous injection of CML. Many small tumors are present on the CAM 7 days after injection of K562 cells into a CAM vessel of an 11 day embryo. The tumors are not easily evident in bright field illumination (12B, left panel), but are easily seen using fluorescence illumination (12B, right panel). The boxed area of (12B) is shown at higher magnification in (12C). Scale bars 100 µm.

Table 1 below summarizes the success rate of tumor formation achieved by the four different methods of transplantation:

| Num. of K562 cells | 0.25*10⁶ | 0.5*10⁶ | 1*10⁶ | 2*10⁶ | 3*10⁶ | 5*10⁶ | 6*10⁶ |
|---|---|---|---|---|---|---|---|
| Inoculation on CAM | 100% | 20% | 23% | — | — | — | — |
| Injection into yolk sac | — | — | — | — | 31.7% | — | 54.2% |
| Injection into amnion | 28.5% | 100% | — | 100% | — | — | — |
| Intravascular injection | — | — | — | — | 100% | 100% | — |

Figure 13A:
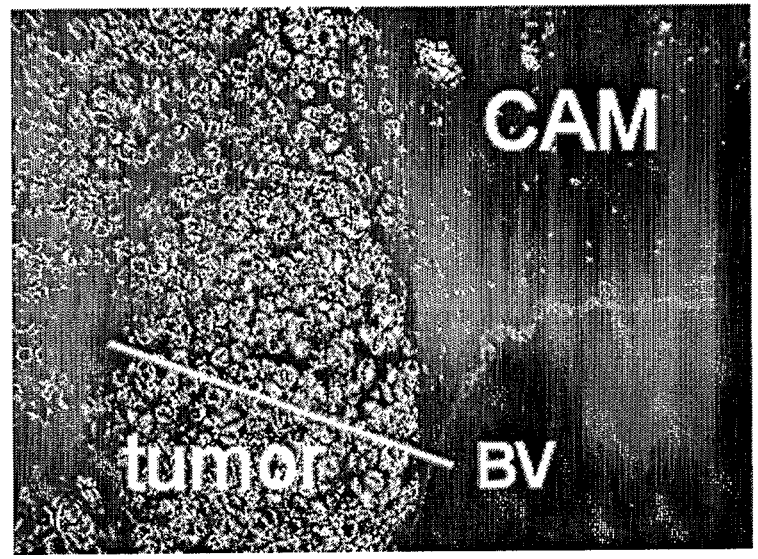
FIG. 13 is an immunocytochemical confirmation that the solid tumor cells in the CAM are of human origin by fixation and staining with mouse anti-human mitochondria antibody (A) and nuclear were stained with Hoecsht (B).
Figure 13B:
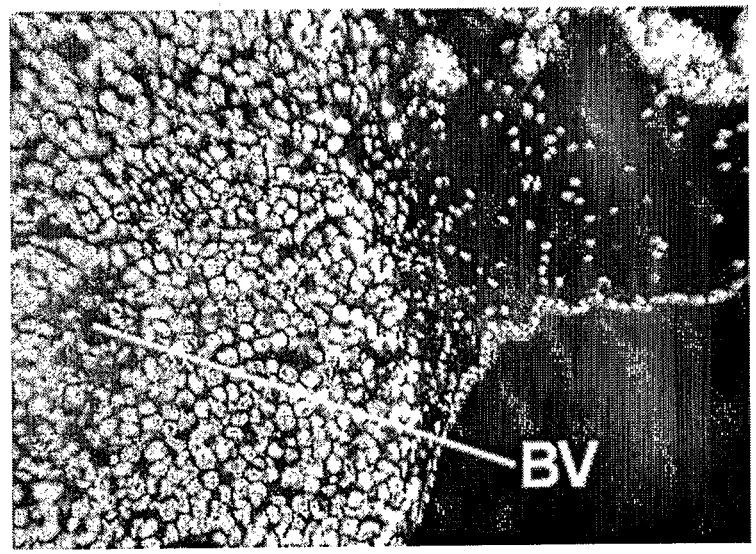

Immunocytochemical confirmation that the solid tumor cells in the CAM are human is shown in FIG. 13. Three million K562 cells were injected into the yolk sac of a 3-days-old chick embryo. Tumors were found on the CAM after 10 days. Tumor was fixed and stained with mouse anti-human mitochondria antibody (A) and nuclear were stained with Hoecsht (B).

Figure 14:
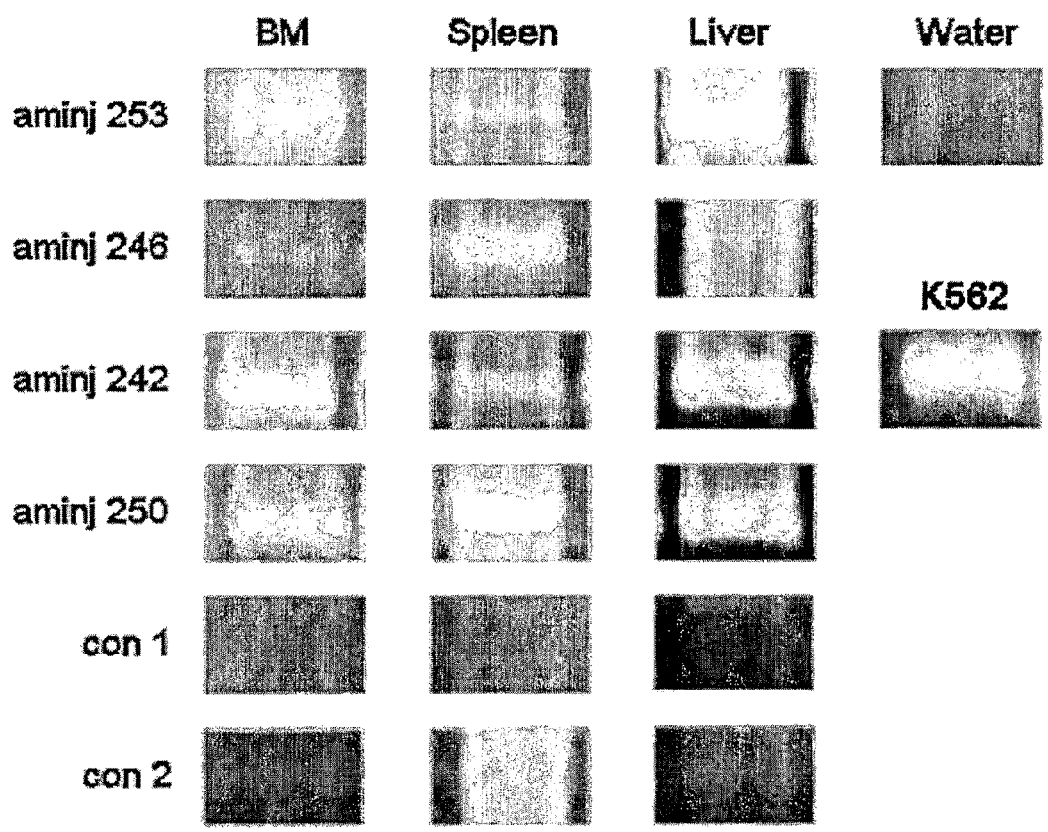
FIG. 14 demonstrates detection of K562 engraftment into multiple hematopoeitic tissues of the chick embryo by PCR.

FIG. 14 demonstrates Engraftment of K562 cells into multiple hematopoeitic tissues of the chick embryo. PCR was performed on genomic DNA extracted from bone marrow (BM), spleen and liver of four embryos (aminj) that received grafts of 0.5-2×10⁶ CML cells, 14 days earlier, and two control embryos (con) of the same age that were not injected. K562 cells were present in all hematopoetic tissues examined in injected, but not in uninjected embryos.

Figure 15:
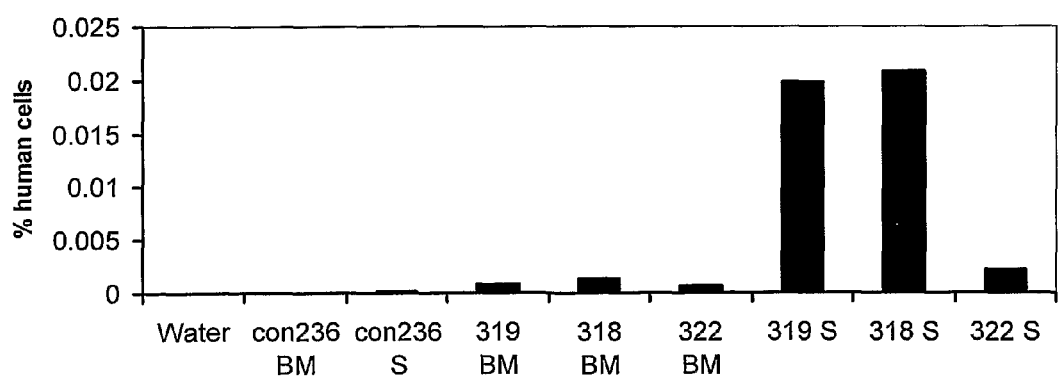
FIG. 15 shows quantitation of K562 engraftment in chick embryos by quantitative PCR.

FIG. 15 demonstrates quantitation of K562 engraftment in chick embryos by quantitative PCR. PCR was performed on genomic DNA extracted from bone marrow (BM) and spleen (S) of embryos that received grafts of 2×10⁶ CML cells to the amnion 14 days earlier, and a PBS-injected control embryo. Human DNA was detected with a satellite DNA probe, and chick DNA with primers for GADPH in the presence of Sybr Green. The engraftment to the spleen was consistently higher than that to the bone marrow, and tissues from all injected embryos were well above background levels in the spleen and BM of the PBS-injected embryo.

Example 11

Enhanced Engraftment of Hematopoietic Cells in Avian Embryos Using Stromal Cells In order to improve the engraftment rate of hematopoietic cells in the avian embryos, human K562 cells are co-cultured with the murine stromal cell line MS-5, and then grafted to chick or turkey embryos intravenously as described in Example 10.

In other experiments, human K562 cells are co-injected with the murine stromal cell line MS-5 to chick embryos intravenously as described in Example 10.

In other experiments, K562 cells are injected into the amnion of early embryos as described in Example 10, and upon the maturation of the CAM a few days later, MS-5 cells are grafted to the CAM for constitutive secretion of leukemia supporting factors to the embryos' blood.

Engraftment is quantified using PCR for human satellite DNA and by FACS as described in Example 10. In addition, engraftment is visually monitored in-vivo by using GFP-expressing leukemia lines as described in Example 10.

Example 12

Toxicity Test for Anti-Leukemia Drugs

For determining drug toxicity, general anti-leukemia agents such as doxorubicin, cytosine arabinoside (ara-C), and targeted therapy such as the anti-tyrosine kinase Glivec (Novartis, currently administered as first line therapy in CML patients), and BMF-354825 (currently undergoing clinical trials) is tested for toxicity in normal, ungrafted embryos.

K562 are injected in the amnion of 3 days old embryos, and 7 days later treatment with 20-40 μg doxorubicin begins for 5 days. Control eggs receive vehicle, which varies according to the specific treatment. Eggs are examined daily for survival of embryos. Initially, at least 20 eggs receive each dose, in parallel with 20 control eggs. After determining which dosage is more appropriate, the dosages is further optimized, and LD50 is calculated. A final series of experiments using dosages that is substantially lower than the one determined to be toxic, applying the drug every other day for 8 days, to determine the toxicity of continued application of the drug.

Example 13

High-Throughput Screening of Anti-Cancer Drugs for Hematopoietic Malignancies

For high-throughput screening of novel chemotherapy drugs, leukemia cells are first treated with a large collection of drugs to be tested in vitro. Depending on the effect of each drug on the cells, i.e., if a drug is capable to reduce the number of the cancer cells by at least 20%, this drug is then selected for the next step, which is in vivo, in the chimeric system. Each drug is then applied to engrafted embryos. In certain experiments, the drugs are applied by injection into the albumin sac. In other experiments, the drugs are applied by injection into the air sac. In yet different experiments, the drugs are applied by dripping on the CAM injection into the yolk sac. In other experiments, the drugs are applied intravenously.

Analysis of the response of the leukemia (the engrafted cells) to treatment is performed using molecular (BCR-Abl and Alu PCR) and protein detection based (FACS, immunocytochemistry and PCR) techniques described above.

In addition, the cellular mechanism of action of the drug is be determined. Propidium iodide, human specific-caspase 3 and TUNEL staining, as well as FACS analysis are used to determine whether the leukemia cells were killed by an apoptotic mechanism. FACS analysis of immunocytochemical staining for blood differentiation markers is performed to determine if the leukemia cells differentiated and therefore ceased their uncontrolled proliferation.

Example 14

Customized Anti-Cancer Drugs to Use in Newly Diagnosed or Relapsed Patients with Hematopoietic Malignancies Samples of patients' blood containing approximately 1×10⁶ leukemia cells are transplanted to avian embryos as described in Examples 10 and 11. After a determined period of time to allow for engraftment, the eggs are treated with several anti-leukemic drugs as described above. The most effective drug is then selected to be used for treatment of the patient from whom the cells were obtained.

Example 15

Turkey embryos were incubated for 11 days in a humid 37° C. incubator. 3 million K562 human leukemia cells engineered to express GFP were injected into a CAM vein via a small window in the eggshell, as described in Example 10 for chick eggs.

Figure 16:
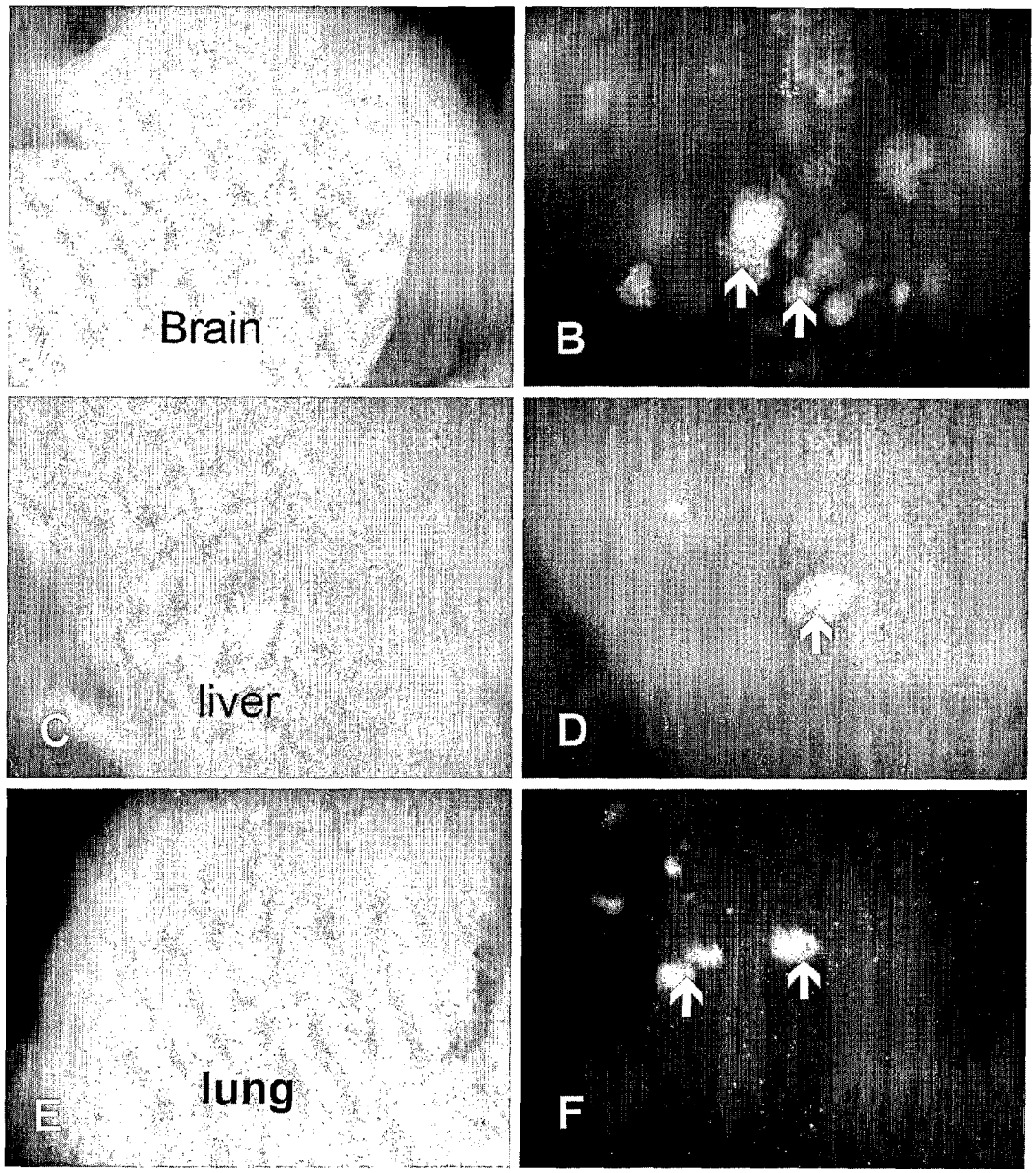
FIG. 16 shows K652 engraftment in several non-hematopoeitic tissues of a turkey embryo.

One week later, the eggs were opened and the embryos removed and examined. As can be seen in FIG. 16, many tissues contained GFP-expressing tumors (several shown at the white arrows) including brain (panels A, B), liver (panels C, D) and lung (panels E, F), as well as skin, bone and spleen. Panels A, C and E are photographed in bright field, panels B, D and F are photographed in fluorescence illumination.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials and steps for carrying out various disclosed functions may take a variety of alternative forms without departing from the invention.

The invention claimed is:

1. A method for screening anti-cancer drugs, comprising:
   a) engrafting a population of malignant mammalian hematopoietic cells into a turkey egg, wherein at least a portion of the malignant mammalian hematopoietic cells are engrafted into at least one hematopoietic tissue of the turkey egg selected from the group consisting of bone marrow, spleen, and liver;
   b) exposing the malignant mammalian hematopoietic cells to at least one test drug; and
   c) analyzing the population of hematopoietic tissue engrafted cells after a determined period of time; thereby screening anti-cancer drugs for hematopoietic malignancies.

2. The method of claim 1, wherein the population of malignant mammalian hematopoietic cells is a population of malignant human hematopoietic cells.

3. The method of claim 2, wherein the malignant human hematopoietic cells are obtained from a subject having a hematopoietic neoplastic disorder.

4. The method of claim 1, wherein said determined period of time is between 1 and 30 days of incubation.

5. The method of claim 1, wherein at least a portion of the malignant mammalian hematopoietic cells is transformed with at least one exogenous nucleic acid sequence.

6. The method of claim 1, wherein the malignant mammalian hematopoietic cells are delivered to the turkey egg in a manner selected from:
   a) injection into the amniotic sac;
   b) injection into the yolk sac;
   c) intravenous injection into the chorioallantoic blood vessels; and
   d) layering the cells on the chorioallantoic membrane.

7. The method of claim 1, further comprises engrafting a second population comprising mammalian stromal cells into said turkey egg, said engrafting a second population is selected from co-engrafting the second population together with the population of malignant mammalian hematopoietic cells, or engrafting prior to or after engraftment of said population of malignant mammalian hematopoietic cells.

8. The method of claim 1, wherein a positive outcome is determined when said test drug reduces at least 50% of the engrafted cells, compared to untreated grafts.

9. The method of claim 3, wherein the hematopoietic neoplastic disorder is selected from the group consisting of: erythroblastic leukemia, acute megakaryoblastic leukemia, myeloproliferative diseases (MPD), polycythemia vera (PV), essential thrombcythemia (ET), acute promyeloid leukemia (APML), acute myelogenous leukemia (AML), chronic myelogenous leukemia (CML), myelodysplastic syndrome (MDS), acute lymphoblastic leukemia (ALL), chronic lymphocytic leukemia (CLL), prolymphocytic leukemia (PLL), hairy cell leukemia (HLL) and Waldenstrom's macroglobulinemia (WM), myeloma, plasmacytoma, plasma cell leukemia, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

10. The method of claim 1, wherein (b) comprises at least one of:
   (i) exposing said hematopoietic cells to said test drug before engraftment of said cells;
   (ii) exposing said hematopoietic cells to said test drug after engraftment of said cells; or
   (iii) exposing said hematopoietic cells to said test drug at specified intervals during culture.

* * * * *